(12) United States Patent　　(10) Patent No.: US 10,180,585 B2
Weeber　　(45) Date of Patent: Jan. 15, 2019

(54) SINGLE MICROSTRUCTURE LENS, SYSTEMS AND METHODS

(71) Applicant: AMO Groningen B.V., Groningen (NL)

(72) Inventor: Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 15/438,628

(22) Filed: Feb. 21, 2017

(65) Prior Publication Data

US 2017/0156849 A1　　Jun. 8, 2017

Related U.S. Application Data

(63) Continuation of application No. 14/589,197, filed on Jan. 5, 2015, now Pat. No. 9,581,834, which is a (Continued)

(51) Int. Cl.
　　*G02C 7/02*　　(2006.01)
　　*A61F 2/16*　　(2006.01)
　　(Continued)

(52) U.S. Cl.
　　CPC .............. *G02C 7/022* (2013.01); *A61B 34/10* (2016.02); *A61F 2/16* (2013.01); *A61F 2/164* (2015.04);
　　(Continued)

(58) Field of Classification Search
　　CPC .......... G02C 7/024; G02C 7/027; G02C 7/04; G02C 7/049
　　(Continued)

(56) References Cited

U.S. PATENT DOCUMENTS 2,077,092 A　　4/1937　Broder
3,305,294 A　　2/1967　Alvarez
(Continued)

FOREIGN PATENT DOCUMENTS

CA　　2722274 A1　　10/2009
CN　　1035363 A　　9/1989
(Continued)

OTHER PUBLICATIONS

Van Den Berg T.J., "Analysis of Intraocular Straylight, Especially in Relation to Age," Optometry and Vision Science, Feb. 1995, vol. 72 (2), pp. 52-59.
(Continued)

*Primary Examiner* — Darryl J Collins
(74) *Attorney, Agent, or Firm* — Johnson & Johnson Surgical Vision, Inc.

(57) ABSTRACT

Systems and methods for providing enhanced image quality across a wide and extended range of foci encompass vision treatment techniques and ophthalmic lenses such as contact lenses and intraocular lenses (IOLs). Exemplary IOL optics can include a circular surface structure which acts as a diffractive or phase shifting profile. In some cases, a single ring IOL includes an anterior face and a posterior face, where a profile can be imposed on the anterior or posterior surface or face. The profile can have an inner portion such as a microstructure or central echelette, and an outer portion. Between the inner portion and the outer portion, there may be a transition zone that connects the inner and outer portions.

15 Claims, 29 Drawing Sheets

Related U.S. Application Data continuation of application No. 13/872,784, filed on Apr. 29, 2013, now Pat. No. 8,926,092, which is a continuation of application No. 12/971,506, filed on Dec. 17, 2010, now Pat. No. 8,430,508.

(60) Provisional application No. 61/288,255, filed on Dec. 18, 2009.

(51) Int. Cl.
| | |
|---|---|
| *G02C 7/04* | (2006.01) |
| *G02C 7/06* | (2006.01) |
| *G02B 27/00* | (2006.01) |
| *A61B 34/10* | (2016.01) |

(52) U.S. Cl.
CPC .......... *A61F 2/1613* (2013.01); *A61F 2/1618* (2013.01); *A61F 2/1645* (2015.04); *A61F 2/1654* (2013.01); *G02B 27/0075* (2013.01); *G02C 7/027* (2013.01); *G02C 7/041* (2013.01); *G02C 7/044* (2013.01); *G02C 7/049* (2013.01); *G02C 7/06* (2013.01); *A61B 2034/104* (2016.02); *A61F 2/1637* (2013.01); *A61F 2230/0006* (2013.01); *G02C 2202/20* (2013.01)

(58) Field of Classification Search
USPC ............. 351/159.01, 159.02, 159.11–159.13, 351/159.15, 159.35, 159.44, 351/159.74–159.77

See application file for complete search history.

(56) References Cited

U.S. PATENT DOCUMENTS

| | | |
|---|---|---|
| 3,367,734 A | 2/1968 | Bystricky et al. |
| 3,735,685 A | 5/1973 | Plummer |
| 4,010,496 A | 3/1977 | Neefe |
| 4,077,071 A | 3/1978 | Freeman |
| 4,093,361 A | 6/1978 | Erickson et al. |
| 4,134,160 A | 1/1979 | Bayers |
| 4,162,122 A | 7/1979 | Cohen |
| 4,174,543 A | 11/1979 | Kelman |
| 4,210,391 A | 7/1980 | Cohen |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A | 3/1982 | Karickhoff |
| 4,338,005 A | 7/1982 | Cohen |
| 4,340,283 A | 7/1982 | Cohen |
| 4,370,760 A | 2/1983 | Kelman |
| 4,377,873 A | 3/1983 | Reichert |
| 4,402,579 A | 9/1983 | Poler |
| 4,403,353 A | 9/1983 | Tennant |
| 4,404,694 A | 9/1983 | Kelman |
| 4,409,691 A | 10/1983 | Levy |
| 4,424,597 A | 1/1984 | Schlegel |
| 4,446,581 A | 5/1984 | Blake |
| 4,480,340 A | 11/1984 | Shepard |
| 4,500,382 A | 2/1985 | Foster |
| 4,504,982 A | 3/1985 | Burk |
| 4,551,864 A | 11/1985 | Akhavi |
| 4,556,998 A | 12/1985 | Siepser |
| 4,560,383 A | 12/1985 | Leiske |
| 4,593,981 A | 6/1986 | Scilipoti |
| 4,605,409 A | 8/1986 | Kelman |
| 4,605,411 A | 8/1986 | Fedorov et al. |
| 4,629,460 A | 12/1986 | Dyer |
| 4,629,462 A | 12/1986 | Feaster |
| 4,636,049 A | 1/1987 | Blaker |
| 4,637,697 A | 1/1987 | Freeman |
| 4,642,112 A | 2/1987 | Freeman |
| 4,655,565 A | 4/1987 | Freeman |
| 4,673,406 A | 6/1987 | Schlegel |
| 4,676,791 A | 6/1987 | Lemaster et al. |
| 4,676,792 A | 6/1987 | Praeger |
| 4,681,102 A | 7/1987 | Bartell |
| 4,687,484 A | 8/1987 | Kaplan |
| 4,687,485 A | 8/1987 | Lim et al. |
| RE32,525 E | 10/1987 | Pannu |
| 4,725,277 A | 2/1988 | Bissonette |
| 4,734,095 A | 3/1988 | Siepser |
| 4,778,462 A | 10/1988 | Grendahl |
| 4,781,717 A | 11/1988 | Grendahl |
| 4,787,903 A | 11/1988 | Grendahl |
| 4,787,904 A | 11/1988 | Severin et al. |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,834,748 A | 5/1989 | McDonald |
| 4,863,539 A | 9/1989 | Lee et al. |
| 4,898,461 A | 2/1990 | Portney |
| 4,932,970 A | 6/1990 | Portney |
| 4,995,714 A | 2/1991 | Cohen |
| 4,995,715 A | 2/1991 | Cohen |
| 4,997,442 A | 3/1991 | Barrett |
| 5,016,977 A | 5/1991 | Baude et al. |
| 5,019,097 A | 5/1991 | Knight et al. |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,078,742 A | 1/1992 | Dahan |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,133,749 A | 7/1992 | Nordan |
| 5,144,483 A | 9/1992 | Cohen |
| 5,147,395 A | 9/1992 | Willis |
| 5,147,397 A | 9/1992 | Christ et al. |
| 5,184,405 A | 2/1993 | Cress |
| 5,197,981 A | 3/1993 | Southard |
| 5,201,763 A | 4/1993 | Brady et al. |
| 5,203,790 A | 4/1993 | McDonald |
| 5,217,491 A | 6/1993 | Vanderbilt |
| 5,225,858 A | 7/1993 | Portney |
| 5,225,997 A | 7/1993 | Lederer et al. |
| 5,229,797 A | 7/1993 | Futhey et al. |
| 5,258,025 A | 11/1993 | Fedorov et al. |
| 5,278,592 A | 1/1994 | Marie et al. |
| 5,408,281 A | 4/1995 | Zhang |
| 5,433,745 A | 7/1995 | Graham et al. |
| 5,476,513 A | 12/1995 | Brady et al. |
| 5,479,220 A | 12/1995 | Komatsu et al. |
| 5,567,365 A | 10/1996 | Weinschenk, III et al. |
| 5,571,177 A | 11/1996 | Deacon et al. |
| 5,620,720 A | 4/1997 | Glick et al. |
| 5,628,796 A | 5/1997 | Suzuki |
| 5,652,638 A | 7/1997 | Roffman et al. |
| 5,691,800 A | 11/1997 | Iki et al. |
| 5,699,142 A | 12/1997 | Lee et al. |
| 5,715,031 A | 2/1998 | Roffman et al. |
| 5,716,403 A | 2/1998 | Tran et al. |
| 5,748,282 A | 5/1998 | Freeman |
| 5,760,871 A | 6/1998 | Kosoburd et al. |
| 5,796,462 A | 8/1998 | Roffman et al. |
| 5,801,807 A | 9/1998 | Satake et al. |
| 5,928,282 A | 7/1999 | Nigam |
| 5,968,094 A | 10/1999 | Werblin et al. |
| 6,015,435 A | 1/2000 | Valunin et al. |
| 6,051,024 A | 4/2000 | Cumming |
| 6,055,111 A | 4/2000 | Nomura et al. |
| 6,126,283 A | 10/2000 | Wen et al. |
| 6,126,286 A | 10/2000 | Portney |
| 6,129,759 A | 10/2000 | Chambers |
| 6,142,625 A | 11/2000 | Sawano et al. |

(56) References Cited

U.S. PATENT DOCUMENTS

| | | |
|---|---|---|
| 6,179,870 B1 | 1/2001 | Sourdille et al. |
| 6,210,005 B1 | 4/2001 | Portney |
| 6,235,055 B1 | 5/2001 | Chu |
| 6,261,321 B1 | 7/2001 | Kellan |
| 6,319,282 B1 | 11/2001 | Nishi |
| 6,338,559 B1 | 1/2002 | Williams et al. |
| 6,419,697 B1 | 7/2002 | Kelman |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,598,606 B2 | 7/2003 | Terwee et al. |
| 6,609,793 B2 | 8/2003 | Norrby et al. |
| 6,705,729 B2 | 3/2004 | Piers et al. |
| 6,709,102 B2 | 3/2004 | Duppstadt |
| 6,802,605 B2 | 10/2004 | Cox et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,899,425 B2 | 5/2005 | Roffman et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 | 11/2008 | Bandhauer et al. |
| 7,455,407 B2 | 11/2008 | Neal et al. |
| 7,475,986 B2 | 1/2009 | Dai et al. |
| 7,615,073 B2 | 11/2009 | Deacon et al. |
| 7,616,330 B2 | 11/2009 | Neal et al. |
| 7,713,299 B2 | 5/2010 | Brady et al. |
| 7,794,497 B2 | 9/2010 | Brady et al. |
| 7,857,451 B2 | 12/2010 | Thibos et al. |
| 7,871,162 B2 | 1/2011 | Weeber |
| 7,993,398 B2 | 8/2011 | Deacon et al. |
| 8,002,827 B2 | 8/2011 | Deacon et al. |
| 8,018,164 B2 | 9/2011 | Shannon et al. |
| 8,231,219 B2 | 7/2012 | Weeber |
| 8,241,354 B2 | 8/2012 | Hong et al. |
| 8,382,281 B2 | 2/2013 | Weeber |
| 8,430,508 B2 | 4/2013 | Weeber |
| 8,480,228 B2 | 7/2013 | Weeber |
| 8,573,775 B2 | 11/2013 | Weeber |
| 8,747,466 B2 | 6/2014 | Weeber et al. |
| 8,770,745 B2 | 7/2014 | Lindacher et al. |
| 8,862,447 B2 | 10/2014 | Weeber |
| 9,335,563 B2 * | 5/2016 | Weeber ............... A61F 2/1637 |
| 2001/0035935 A1 | 11/2001 | Bhalakia et al. |
| 2001/0051825 A1 | 12/2001 | Peterson |
| 2002/0118337 A1 | 8/2002 | Perrott et al. |
| 2002/0173846 A1 | 11/2002 | Blake et al. |
| 2002/0196408 A1 | 12/2002 | Bhalakia et al. |
| 2002/0196412 A1 | 12/2002 | Abitbol |
| 2003/0076478 A1 | 4/2003 | Cox |
| 2003/0171808 A1 | 9/2003 | Phillips |
| 2004/0054358 A1 | 3/2004 | Cox |
| 2004/0068317 A1 | 4/2004 | Knight |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150790 A1 | 8/2004 | Roffman et al. |
| 2004/0156014 A1 | 8/2004 | Piers et al. |
| 2004/0167622 A1 | 8/2004 | Sunalp et al. |
| 2005/0096226 A1 | 5/2005 | Stock et al. |
| 2005/0125056 A1 | 6/2005 | Deacon et al. |
| 2005/0128432 A1 | 6/2005 | Altmann |
| 2005/0203619 A1 | 9/2005 | Altmann |
| 2005/0251254 A1 | 11/2005 | Brady et al. |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0066808 A1 | 3/2006 | Blum et al. |
| 2006/0068453 A1 | 3/2006 | Altieri |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0238702 A1 | 10/2006 | Glick et al. |
| 2006/0244904 A1 | 11/2006 | Hong et al. |
| 2006/0244916 A1 | 11/2006 | Guillon |
| 2006/0279700 A1 | 12/2006 | Liang |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0018910 A1 | 1/2008 | Neal et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0231809 A1 | 9/2008 | Haigis |
| 2008/0269642 A1 | 10/2008 | Deacon et al. |
| 2008/0273169 A1 | 11/2008 | Blum et al. |
| 2008/0291393 A1 | 11/2008 | Menezes |
| 2009/0012609 A1 | 1/2009 | Geraghty et al. |
| 2009/0036980 A1 | 2/2009 | Norrby et al. |
| 2009/0051876 A1 | 2/2009 | Seiler et al. |
| 2009/0062911 A1 | 3/2009 | Bogaert |
| 2009/0088840 A1 | 4/2009 | Simpson et al. |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0279048 A1 | 11/2009 | Hong et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0100178 A1 | 4/2010 | Weeber et al. |
| 2010/0130888 A1 | 5/2010 | Deacon et al. |
| 2010/0161048 A1 | 6/2010 | Schaper, Jr. |
| 2010/0274234 A1 | 10/2010 | Liang |
| 2012/0140166 A1 | 6/2012 | Zhao |
| 2012/0320334 A1 | 12/2012 | Ho et al. |

FOREIGN PATENT DOCUMENTS

| | | |
|---|---|---|
| CN | 1039487 A | 2/1990 |
| CN | 1406120 A | 3/2003 |
| CN | 1833192 A | 9/2006 |
| DE | 8107675 U1 | 7/1981 |
| EP | 226400 A2 | 6/1987 |
| EP | 227357 A2 | 7/1987 |
| EP | 0343067 A1 | 11/1989 |
| EP | 0457553 A2 | 11/1991 |
| EP | 681198 A1 | 11/1995 |
| EP | 0926531 A1 | 6/1999 |
| EP | 949529 A2 | 10/1999 |
| EP | 957331 A2 | 11/1999 |
| EP | 1424049 A1 | 6/2004 |
| EP | 1310267 B1 | 1/2008 |
| EP | 1424049 B1 | 6/2009 |
| EP | 2182891 B1 | 4/2014 |

(56) References Cited

FOREIGN PATENT DOCUMENTS

| | | |
|---|---|---|
| FR | 2745711 A1 | 9/1997 |
| JP | H0255314 A | 2/1990 |
| WO | 8603961 A1 | 7/1986 |
| WO | 9222264 A1 | 12/1992 |
| WO | 9303409 A1 | 2/1993 |
| WO | 9507487 A1 | 3/1995 |
| WO | 9856315 A1 | 12/1998 |
| WO | 0019906 A1 | 4/2000 |
| WO | 0111418 A1 | 2/2001 |
| WO | 0135868 A1 | 5/2001 |
| WO | 0154569 A1 | 8/2001 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03009053 A1 | 1/2003 |
| WO | 2004034129 A1 | 4/2004 |
| WO | 04090611 A2 | 10/2004 |
| WO | 04096014 A2 | 11/2004 |
| WO | 05019906 A1 | 3/2005 |
| WO | 06025726 A1 | 3/2006 |
| WO | 2006032263 A2 | 3/2006 |
| WO | 06047698 A1 | 5/2006 |
| WO | 06060477 A2 | 6/2006 |
| WO | 06060480 A2 | 6/2006 |
| WO | 2007067872 A2 | 6/2007 |
| WO | 2007092948 A1 | 8/2007 |
| WO | 2007133384 A2 | 11/2007 |
| WO | 2008045847 A2 | 4/2008 |
| WO | 2008083283 A2 | 7/2008 |
| WO | 2009020963 A1 | 2/2009 |
| WO | 2009029515 A1 | 3/2009 |
| WO | 2009058755 A1 | 5/2009 |
| WO | 2009076670 A1 | 6/2009 |
| WO | 2009137491 A1 | 11/2009 |
| WO | 2010009254 A1 | 1/2010 |
| WO | 2010009257 A1 | 1/2010 |

OTHER PUBLICATIONS

Van Meeteren A., "Calculations on the Optical Modulation Transfer Function of the Human Eye for White Light," Optica Acta, May 1974, vol. 21 (5), pp. 395-412.
Vass C., et al., "Prediction of Pseudophakic Capsular bag Diameter based on Biometric Variables," Journal of Cataract and Refractive Surgery, 1999, vol. 25 (10), pp. 1376-1381.
Villegas E.A., et al., "Correlation between Optical and Psychophy, Sical Parameters as a Function of Defocus," Optometry and Vision Science, Jan. 1, 2002, vol. 79 (1), pp. 60-67.
Alfonso J.F., et al., "Prospective Study of the Acri.LISA Bifocal Intraocular Lens," Journal of Cataract Refractive Surgery, Nov. 2007, vol. 33 (11), pp. 1930-1935.
Alio J.L., et al., "Phakic Anterior Chamber Lenses for the Correction of Myopia: A 7-Year Cumulative Analysis of Complications in 263 Cases," Ophthalmology, 1999, vol. 106 (3), pp. 458-466.
Apple D.J., et al., "Anterior Chamber Lenses Part 1: Complications and Pathology and a Review of Designs," Journal of Cataract Refractive Surgery, 1987, vol. 13 (2), pp. 157-174.
Apple D.J., et al., Eds., "Intraocular Lenses: Evolution, Designs, Complications and Pathology," in: New Concepts in Intraocular Lens Implantation, Williams & Wilkins publisher, 1989, vol. 36 (1), pp. 21-36.
Apple D.J., et al., Eds., "Intraocular Lenses: Evolution, Designs, Complications and Pathology," in: New Concepts in Intraocular Lens Implantation, Williams & Wilkins publisher, 1989, vol. 22 (36), pp. 205-221.
Baikoff G., et al., "Angle-fixated Anterior Chamber Phakic Intraocular Lens for Myopia 7 to −19 Diopters," Journal of Refractive Surgery, 1998, vol. 14 (3), pp. 282-292.
Canovas C., et al., "Hybrid Adaptive-Optics Visual Simulator," Optical Letters, Jan. 15, 2010, vol. 35 (2), pp. 196-198.
Cheng X., et al., "Predicting Subjective Judgment of Best Focus with Objective Image Quality Metrics," Journal of Vision, 2004, vol. 4 (4), pp. 310-321.
CILCO Advertisement Brochure, Oct. 1982, 3 pages.
Cohen A.L., "Practical Design of a Bifocal Hologram Contact Lens or Intraocular Lens," Applied Optics, Jul. 1, 1992, vol. 31 (19), pp. 3750-3754.
Co-pending U.S. Appl. No. 11/618,325, filed Dec. 29, 2006.
Co-pending U.S. Appl. No. 11/618,411, filed Dec. 29, 2006.
De Almeida M.S., et al., "Different Schematic Eyes and their Accuracy to the in Vivo Eye: A Quantitative Comparison Study," Brazilian Journal of Physics, 2007, vol. 37 (2A), 10 pages.
Diffractive Lenses for Extended Depth of Focus and Presbyopic Correction, Presentation from Wavefront Congress held on Feb. 15, 2008, Rochester, New York.
Doskolovich L.L., et al., "Special Diffractive Lenses," Lens and Optical Systems Design, Apr. 1992, vol. 1780, pp. 393-402.
European Search Report for Application No. EP11165087, dated Jul. 22, 2011, 6 pages.
European Search Report for Application No. EP89304883, dated Sep. 3, 1990, 1 page.
International Search Report and Written Opinion for Application No. PCT/IB2011/001067, dated Sep. 13, 2011, 13 pages.
International Search Report and Written opinion for Application No. PCT/US08/061180, dated Sep. 5, 2008, 10 pages.
International Search Report and Written opinion for Application No. PCT/US09/038469, dated Aug. 10, 2009, 12 pages.
International Search Report and Written Opinion for Application No. PCT/US2011/026193, dated Jun. 7, 2011, 17 pages.
International Search Report for Application No. PCT/EP2008/061235, dated Mar. 5, 2009, 2 pages.
International Search Report for Application No. PCT/EP2009/051783, dated Apr. 28, 2009, 4 pages.
International Search Report for Application No. PCT/IB2009/005590, dated Sep. 30, 2009, 3 pages.
International Search Report for Application No. PCT/US08/073999, dated Dec. 3, 2008, 3 pages.
International Search Report for Application No. PCT/US09/042449, dated Nov. 5, 2009, 5 pages.
International Search Report for Application No. PCT/US2009/034555, dated May 18, 2009, 6 pages.
International Search Report for Application No. PCT/US2010/038167, dated Sep. 27, 2010, 2 pages.
International Search Report for Application No. PCT/US2010/061017, dated Jun. 16, 2011, 7 pages.
International Search Report for Application No. PCT/US2010/061042, dated Mar. 31, 2011, 3 pages.
International Search Report for Application No. PCT/US2010/061081, dated Jun. 6, 2011, 7 pages.
International Search Report for Application No. PCT/US2011/043119, dated Feb. 15, 2012, 6 pages.
Kim J.H., et al., "The Analysis of Predicted Capsular Bag Diameter using Modified Model of Capsule Measuring Ring in Asians," Clinical and Experimental Ophthalmology, 2008, vol. 36 (3), pp. 238-244.
Liou H.L., et al., "Anatomically Accurate, Finite Model Eye for Optical Modeling," Journal of Optical Society of America, Aug. 1997, vol. 14 (8), pp. 1684-1695.
Liou H.L., et al., "The Prediction of Spherical Aberration with Schematic Eyes," Ophthalmic and Physiological Optics, Jan. 1996, vol. 16 (4), pp. 348-354.
Marinho A., "Results are Encouraging for Phakic IOLs, but More Work is needed," Refractive Surgery, 2000, p. 12, 15.
Marsack J.D., et al., "Metrics of Optical Quality Derived from Wave Aberrations Predict Visual Performance," Journal of Vision, Apr. 2004, vol. 4 (4), pp. 322-328.
Menapace R., "The Capsular Tension Rings," Journal of Cataract & Refractive Surgery, 2008, Chap. 3, pp. 27-44.
Monsoriu J.A., et al., "Devil's Lenses," Optics Express, Oct. 17, 2007, vol. 15 (21), pp. 13858-13864.
Navarro R., et al., "Accommodation-Dependent Model of the Human Eye with Aspherics," Journal of the Optical Society of America, 1985, vol. 2 (8), pp. 1273-1281.

(56) References Cited

OTHER PUBLICATIONS

Nio Y.K., et al., "Effect of Intraocular Lens Implantation on Visual Acuity, Contrast Sensitivity, and Depth of Focus," Journal of Cataract and Refractive Surgery, 2003, vol. 29 (11), pp. 2073-2081.
Norrby S., et al., "Model Eyes for Evaluation of Intraocular Lenses," Applied Optics, Sep. 7, 2007, vol. 46 (26), pp. 6595-6605.
Olsen T., "Simple Method to Calculate the Surgically Induced Refractive Change," Journal of Cataract & Refractive Surgery, 1993, vol. 19 (2), pp. 319-320.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Praeger D.L., "Praeger Technique for the Insertion of the Copeland Radial IOL Posterior Chamber Placement," Copeland Lens, 1982, 7 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Strenn K., et al., "Capsular bag Shrinkage after Implantation of an Open-Loop Silicone Lens and a Poly(methyl methacrylate) Capsule Tension Ring," Journal of Cataract and Refractive Surgery, 1997, vol. 23 (10), pp. 1543-1547.
Tehrani M., et al., "Capsule Measuring Ring to Predict Capsular Bag Diameter and Follow its Course after Foldable Intraocular Lens Implantation," Journal of Cataract Refractive Surgery, 2003, vol. 29 (11), pp. 2127-2134.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Venter, J.A., et al., "Visual Outcomes and Patient Satisfaction with a Rotational Asymmetric Refractive Intraocular Lens for Emmetropic Presbyopia," Cataract & Refractive Surgery, Mar. 2015, vol. 41 (3), pp. 585-593.

\* cited by examiner

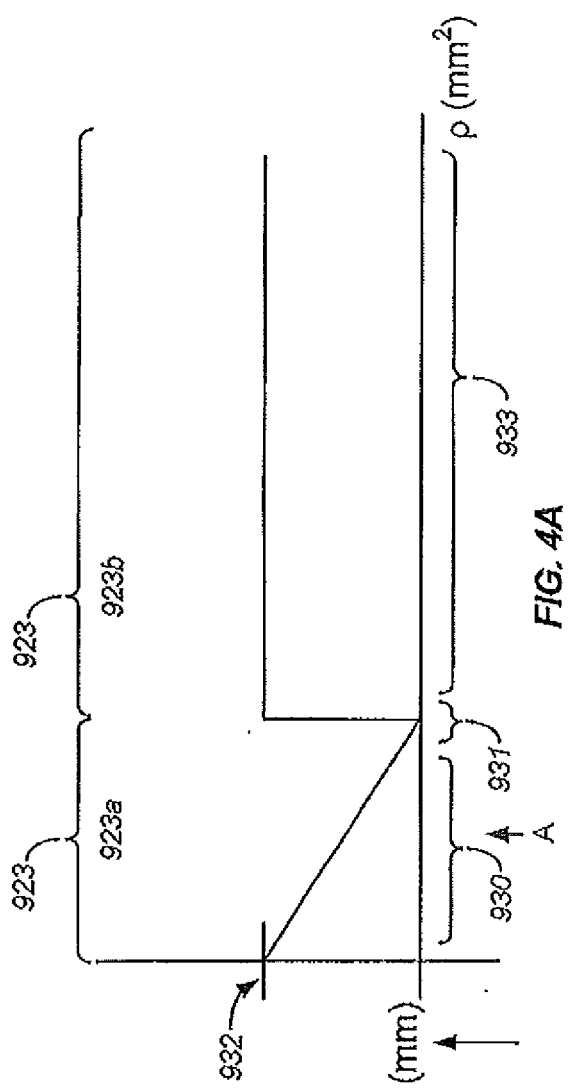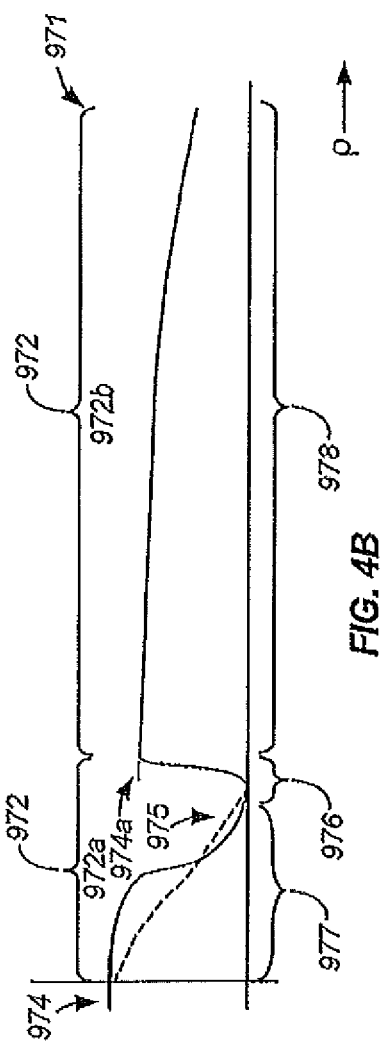

1D add, 100%

2D add, 10%

Sample 2.0D / 30% aspherical monofocal

Refractive bifocal +1D add power

Diffractive multifocal +4D add power

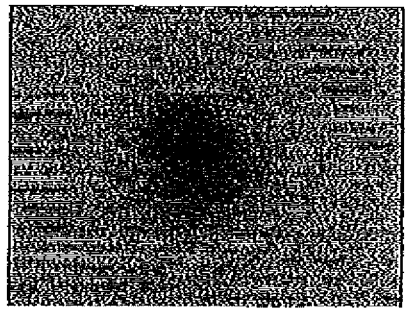
FIG. 23A-2  Sample 2.0D / 30%
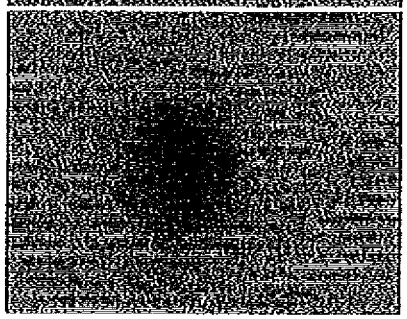
FIG. 23B-2  aspherical monofocal
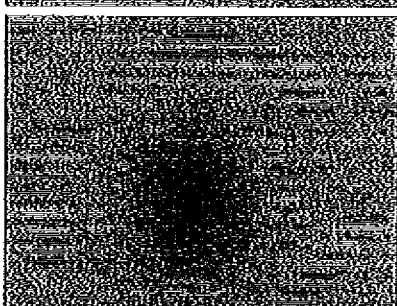
FIG. 23C-2  Refractive bifocal +1D add power
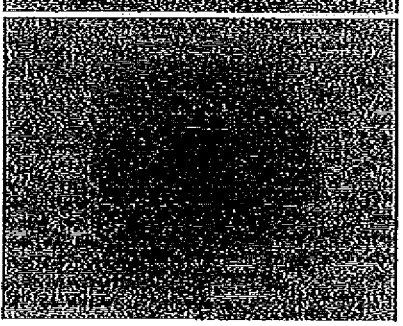
FIG. 23D-2  Diffractive multifocal +4D add power

SINGLE MICROSTRUCTURE LENS, SYSTEMS AND METHODS

CROSS-REFERENCES TO RELATED APPLICATIONS

This application is a continuation of and claims priority to U.S. application Ser. No. 14/589,197, filed Jan. 5, 2015, which is a continuation application and claims priority to U.S. application Ser. No. 13/872,784, entitled "Single Microstructure Lens, Systems and Methods", filed on Apr. 29, 2013 and issued as U.S. Pat. No. 8,926,092, which is a continuation application and claims priority to U.S. application Ser. No. 12/971,506, entitled "Single Microstructure Lens, Systems and Methods", filed on Dec. 17, 2010 and issued as U.S. Pat. No. 8,430,508, which claims priority under 35 U.S.C. § 119(e) to provisional application No. 61/288,255 filed on Dec. 18, 2009, the entire contents of which are incorporated herein by reference. This application is related to the following applications which were filed concurrently herewith: Limited Echelette Lens, Systems And Methods, U.S. patent application Ser. No. 12/971,607, filed on Dec. 17, 2010; Ophthalmic Lens, Systems And Methods With Angular Varying Phase Delay, U.S. patent application Ser. No. 12/971,889, filed on Dec. 17, 2010; and Ophthalmic Lens, Systems And Methods Having At Least One Rotationally Asymmetric Diffractive Structure, U.S. Patent Application No. 61/424,433, filed on Dec. 17, 2010. The entire contents of these three applications are also incorporated herein by reference. This application is also related to the following U.S. patent application Ser. No. 61/047,699 and Ser. No. 12/109,251, both filed on Apr. 24, 2008; Ser. No. 12/429,155 filed on Apr. 23, 2009; Ser. No. 12/372,573 filed on Feb. 17, 2009; Ser. No. 12/197,249 filed on Aug. 23, 2008; Ser. No. 12/120,201 filed on Apr. 13, 2008, and Ser. No. 12/771,550 filed on Apr. 30, 2010.

BACKGROUND OF THE INVENTION

Embodiments of the present invention relate to vision treatment techniques and in particular, to ophthalmic lenses such as, for example, contact lenses, corneal inlays or onlays, or intraocular lenses (IOLs) including, for example, phakic IOLs and piggyback IOLs (i.e. IOLs implanted in an eye already having an IOL).

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only a limited ability to change shape.

Along with reductions in accommodation of the eye, age may also induce clouding of the lens due to the formation of a cataract. A cataract may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

Monofocal IOLs are intended to provide vision correction at one distance only, usually the far focus. Predicting the most appropriate IOL power for implantation has limited accuracy, and an inappropriate IOL power can leave patients with residual refraction errors following surgery. Accordingly, it may be necessary for a patient who has received an IOL implant to also wear spectacles to achieve good far vision. At the very least, since a monofocal IOL provides vision treatment at only one distance and since the typical correction is for far distance, spectacles are usually needed for good near and sometimes intermediate vision. The term "near vision" generally corresponds to vision provided when objects are at a distance from the subject eye of between about 1 to 2 feet are substantially in focus on the retina of the eye. The term "distant vision" generally corresponds to vision provided when objects at a distance of at least about 6 feet or greater are substantially in focus on the retina of the eye. The term "intermediate vision" corresponds to vision provided when objects at a distance of about 2 feet to about 5 feet from the subject eye are substantially in focus on the retina of the eye.

There have been various attempts to address limitations associated with monofocal IOLs. For example, multifocal IOLs have been proposed that deliver, in principle, two foci, one near and one far, optionally with some degree of intermediate focus. Such multifocal, or bifocal, IOLs are intended to provide good vision at two distances, and include both refractive and diffractive multifocal IOLs. In some instances, a multifocal IOL intended to correct vision at two distances may provide a near add power of about 3.0 or 4.0 diopters.

Multifocal IOLs may, for example, rely on a diffractive optical surface to direct portions of the light energy toward differing focal distances, thereby allowing the patient to clearly see both near and far objects. Multifocal ophthalmic lenses (including contact lenses or the like) have also been proposed for treatment of presbyopia without removal of the natural crystalline lens. Diffractive optical surfaces, either monofocal or multifocal, may also be configured to provide reduced chromatic aberration.

Diffractive monofocal and multifocal lenses can make use of a material having a given refractive index and a surface curvature which provide a refractive power. Diffractive lenses have a diffractive profile which confers the lens with a diffractive power that contributes to the overall optical power of the lens. The diffractive profile is typically characterized by a number of diffractive zones. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different add powers. Together, these echelettes form a diffractive profile.

A multifocal diffractive profile of the lens may be used to mitigate presbyopia by providing two or more optical powers; for example, one for near vision and one for far vision. The lenses may also take the form of an intraocular lens placed within the capsular bag of the eye, replacing the original lens, or placed in front of the natural crystalline lens. The lenses may also be in the form of a contact lens, most commonly a bifocal contact lens, or in any other form mentioned herein.

Although multifocal ophthalmic lenses lead to improved quality of vision for many patients, additional improvements would be beneficial. For example, some pseudophakic patients experience undesirable visual effects (dysphotopsia), e.g. glare or halos. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. Another area of improvement revolves around the typical bifocality of multifocal lenses. Since multifocal ophthalmic lenses typically provide for near and far vision, intermediate vision may be compromised.

A lens with an extended depth of focus may thus provide certain patients the benefits of good vision at a range of distances, while having reduced or no dysphotopsia. Various techniques for extending the depth of focus of an IOL have been proposed. For example, some approaches are based on a bulls-eye refractive principle, and involve a central zone with a slightly increased power. Other techniques include an asphere or include refractive zones with different refractive zonal powers.

Although certain proposed treatments may provide some benefit to patients in need thereof, further advances would be desirable. For example, it would be desirable to provide improved IOL systems and methods that confer enhanced image quality across a wide and extended range of foci without dysphotopsia. Embodiments of the present invention provide solutions that address the problems described above, and hence provide answers to at least some of these outstanding needs.

BRIEF SUMMARY OF THE INVENTION

Embodiments of the present invention generally provide improved lenses and imaging techniques. Exemplary embodiments provide improved ophthalmic lenses (such as, for example, contact lenses, corneal inlays or onlays, or intraocular lenses (IOLs) including, for example, phakic IOLs and piggyback IOLs) and associated methods for their design and use.

Embodiments of the present invention encompass IOL optics having a singular circular surface structure, which acts as a phase shifting profile. The profile is designed such that it increases the depth of focus of the pseudophakic eye, where the natural crystalline lens of the eye is substituted with a synthetic lens. Such a singular IOL technique suppresses the distinct bifocality associated with traditional multifocal IOLs which have many diffractive rings. Consequently, dysphotopsia (e.g., halo effects) associated with traditional multifocal IOLs can be alleviated by lenses according to embodiments of the present invention.

An exemplary single ring IOL includes an anterior face and a posterior face. A profile can be imposed on the anterior or posterior surface or face. The profile can have an inner portion and an outer portion. The inner portion typically presents a parabolic curved shape. The inner portion may also be referred to as a microstructure, an isolated echelette, or a central echelette. Between the inner portion and the outer portion, there may be a transition zone that connects the inner and outer portions.

In addition to parabolic shapes, the central echelette can have any of a variety of shapes including hyperbolic, spherical, aspheric, and sinusoidal. The transition between the inner and outer portions of the echelette can be a sharp transition or it can be a smooth transition.

The surface of the outer portion at the outside of the microstructure can have any spherical or aspherical shape. The shape of the outer portion can be optimized for having the desired optical performance for a range of pupil sizes. The desired optical performance can be based on elements such as the depth of focus, the optical quality in the far focus, and the change in best focus (or far focus) position as a function of the pupil size. Optimization rules may be applied as if the shape were a refractive monofocal IOL, or a refractive IOL having an extended depth of focus, or a refractive design that corrects or modifies the ocular spherical aberration. Specific designs can be made in which the interplay between the central echelette and the outer zone is incorporated in the design or optimization. The techniques described herein are well suited for implementation with any of a variety of ophthalmic lenses, including IOLs, corneal inlays or onlays, and/or contact lenses.

In one aspect, embodiments of the present invention encompass ophthalmic lens systems and methods for treating an eye of a patient. An exemplary lens may include an anterior face with an anterior refractive profile and a posterior face with a posterior refractive profile. The faces may be disposed about an optical axis. The lens may also include a diffractive profile imposed on the anterior refractive profile, on the posterior refractive profile, or on both. In an exemplary embodiment, a diffractive profile may include no more than one echelette. Optionally, the echelette can be disposed within a central zone of the lens. Relatedly, the echelette may be positioned as an annulus surrounding a central refractive zone of the lens. In some cases, the lens includes a peripheral zone that surrounds the echelette or annular ring. The echelette may be characterized by a constant phase shift.

According to some embodiments, an ophthalmic lens can include an echelette that is characterized by a parabolic curve. An echelette can have a diameter within a range from about 1 mm to about 4 mm. For example, an echelette may have a diameter of about 1.5 mm. In some cases, an echelette can have a diameter within a range from about 1.0 mm to about 5.0 mm. The echelette can have a surface area that is between 1 and 7 mm$^2$. Preferably, the echelette can have a surface area that is between 1.5 and 4 mm$^2$. For example, the echelette may have a surface area that is 2.3 mm$^2$.

Lens embodiments may include a peripheral portion characterized by a spherical curve or an aspherical curve. In some cases, the peripheral portion can be refractive. A lens may include a peripheral portion having an outer diameter within a range from about 4 mm to about 7 mm. For example, a lens may include a peripheral portion having an outer diameter of about 5 mm.

A lens may include a transition characterized by a step height having a value within a range from about 0.5 µm and about 4 µm. According to some embodiments, a transition can be characterized by a step height having a value within a range of about 1.5 µm and 2.5 µm. According to some embodiments, a transition can be characterized by a step height having a value of about 1.7 µm. In other embodiments, the step height may have a value of about 2.0 µm.

The extended depth of focus may be based on a relative threshold over a range of foci. For instance, image quality may be presented by the volume under the white-light MTF curve, as a percentage of the volume under the white-light diffraction limited MTF ("MTF volume"). In some cases, a lens can provide an MTF volume of at least about 35% throughout a continuous range from about −1.25 D to about 0.25 D for a 2.0 mm pupil. In other words, a lens can provide an MTF volume of at least 35% over a continuous range of at least about 1.5 D. Certain embodiments of the present invention provide for an MTF volume of at least 35% over a continuous range of at least about 0.75 D. Other embodiments can provide an MTF volume of at least 35% over a continuous range of at least about 1.0 D. More preferably, embodiments can provide an MTF volume of at least 35% over a continuous range of at least 1.25 D. In some cases, a lens can provide an MTF at 50 cycles per millimeter of at least 15 over a continuous range of at least about 1.5 D. Certain embodiments provide an MTF at 50 cycles per millimeter of at least 15 over a continuous range of at least 1.0 D. In other cases, a lens can provide an MTF at 100 cycles per millimeter of at least 7 over a range of at least about 1.8 D. Certain embodiments provide an MTF at 100 cycles per millimeter of at least 7 over a continuous range of at least 1.5 D.

In some cases, a diffractive profile can be characterized by a design wavelength, and a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength. According to some embodiments the lens may include a transition characterized by a step height producing a phase shift of about 0.5. In other embodiments, the lens may include a transition characterized by a step height of about 0.4.

In another aspect, embodiments of the present invention encompass systems and methods that involve an ophthalmic lens having a diffractive primary zone that presents a base diffractive surface having a purely optical function, and a refractive peripheral zone that surrounds the diffractive primary zone. An ophthalmic lens may also include a transition zone that physically connects the diffractive primary zone with the refractive peripheral zone. The transition zone may optionally provide optical characteristics.

For a fuller understanding of the nature and advantages of the present invention, reference should be had to the ensuing detailed description taken in conjunction with the accompanying drawings.

BRIEF DESCRIPTION OF THE DRAWINGS

FIGS. 4A-4B illustrate aspects of a lens profile according to embodiments of the present invention.

FIG. 4C depicts aspects of a profile of a lens according to embodiments of the present invention.

FIGS. 23A-1 to 23D-2 show aspects of dysphotopsia performance according to embodiments of the present invention.

Figure 1A:
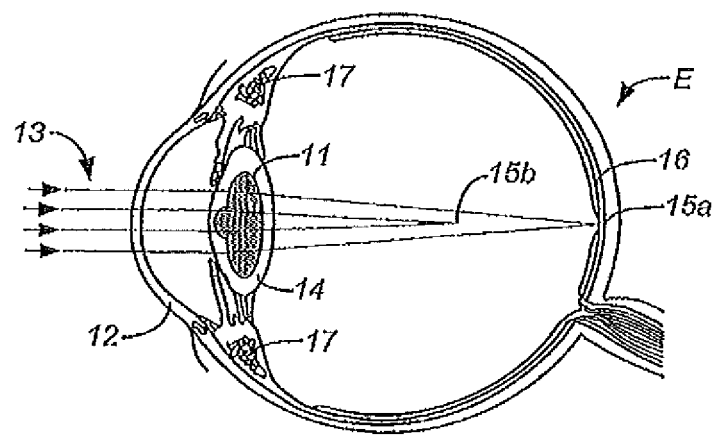
FIG. 1A is a cross-sectional view of an eye with a multifocal refractive intraocular lens.

For illustration purposes, the profile geometries shown in certain aforementioned figures were not drawn exactly to scale. The heights of the profiles shown in the figures are generally on the order of about 0.5 μm to about 8.0 μm although the heights may vary depending on factors such as the amount of correction needed by the patient, the refractive index of the lens material and surrounding medium, and the desired phase shift/delay.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity and brevity, many other elements found in typical ophthalmic lenses, implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments of the present invention encompass systems and methods that provide improved image quality over an extended range of focal points or foci. Systems and methods disclosed herein can encompass various ophthalmic lenses such as, for example, contact lenses, intraocular lenses, spectacle lenses, and corneal inlays or onlays. Exemplary embodiments include ophthalmic lenses having an extended depth of focus, as compared to conventional monofocal lenses, and reduced dysphotopsia as compared to conventional multifocal ophthalmic lenses. In some cases, such techniques involve an IOL approach that includes a single ring, or echelette, and typically involves an expanded depth of focus. Advantageously, such approaches can provide a patient with good distance vision, as well as good vision at intermediate distances without dysphotopsia.

Embodiments of the present invention generally provide improved lenses and imaging systems and may be incorporated into any system in which a lens with an extended depth of focus may be advantageous, such as camera/video lenses, including those used for surveillance or for surgical procedures, as well as for cameras in mobile phones or other related devices. Embodiments of the invention may find their most immediate use in the form of improved ophthalmic devices, systems, and methods. Exemplary embodiments of the present invention provide improved ophthalmic lenses (including, for example contact lenses, intraocular lenses (IOLs), corneal implants and the like) and associated methods for their design and use. Embodiments of the present invention may be used with monofocal diffractive or refractive lenses, bifocal diffractive or refractive lenses, and multifocal diffractive or refractive lenses, e.g. embodiments of the present invention could be added to the opposite surface of multifocal IOLs, e.g. TECNIS Multifocal, REZOOM, or RESTOR IOLs. In other words, an extended depth of focus feature may be added to, for example, the opposite surface of a diffractive or refractive multifocal embodiment. In addition, an extended depth of focus feature may be added to, for example, a toric IOL, an IOL that modifies ocular spherical and/or chromatic aberration, and/ or an accommodating IOL. In general, an extended depth of focus feature may be added to an IOL that modifies ocular aberrations.

Reading is often done in bright light conditions in which the pupil is small. In contrast, night-time driving is done in low light conditions in which the pupil is large. Embodiments of the present invention encompass lenses that relatively emphasize intermediate or near vision for small pupil sizes, while also relatively emphasizing far vision for large pupil sizes. In some such ophthalmic lenses, a greater proportion of light energy may be transmitted to the far focus from a peripheral portion of the lens to accommodate for low light, far viewing conditions such as night time driving; the near or intermediate focus may receive relatively more light energy than a central portion of the diffractive profile—for reading or computer work for example and/or to provide depth of focus and intermediate or near viewing under low light reading conditions as in for example reading restaurant menus.

FIG. 1A is a cross-sectional view of an eye E fit with a multifocal IOL 11. As shown, multifocal IOL 11 may, for example, comprise a bifocal IOL. Multifocal IOL 11 receives light from at least a portion of cornea 12 at the front of eye E and is generally centered about the optical axis of eye E. For ease of reference, FIGS. 1A and 1B do not disclose the refractive properties of other parts of the eye, such as the corneal surfaces. Only the refractive and/or diffractive properties of the multifocal IOL 11 are illustrated.

Each major face of lens 11, including the anterior (front) surface and posterior (back) surface, generally has a refractive profile, e.g. biconvex, plano-convex, plano-concave, meniscus, etc. The two surfaces together, in relation to the properties of the surrounding aqueous humor, cornea, and other optical components of the overall optical system, define the effects of the lens 11 on the imaging performance by eye E. Conventional, monofocal IOLs have a refractive power based on the refractive index of the material from which the lens is made, and also on the curvature or shape of the front and rear surfaces or faces of the lens.

In a young healthy eye, contraction and relaxation of ciliary muscles 17 surrounding the capsular bag 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore conventionally use corrective optics having two optical powers, one for near vision and one for far vision, as provided by multifocal IOL 11.

Multifocal lenses may optionally also make special use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a higher surface curvature and a generally higher overall power (sometimes referred to as a positive add power) suitable for viewing at near distances.

Figure 1B:
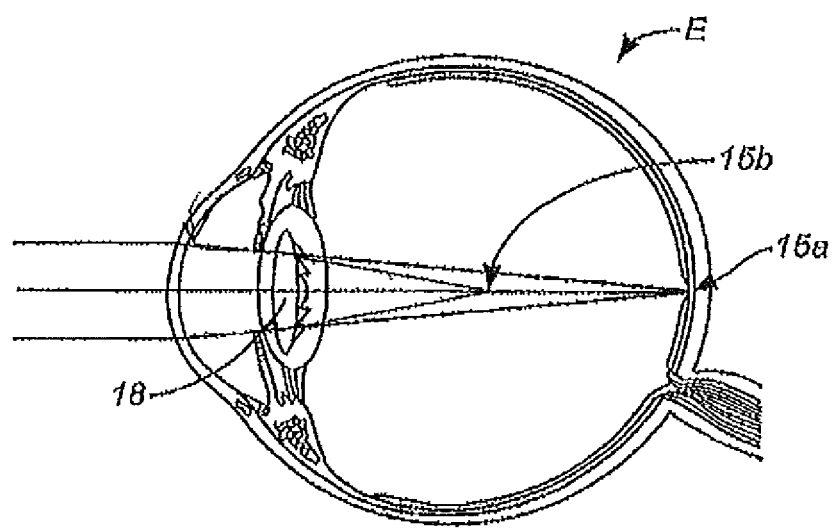
FIG. 1B is a cross-sectional view of an eye having an implanted multifocal diffractive intraocular lens.

Rather than relying entirely on the refractive properties of the lens, multifocal diffractive IOLs or contact lenses can also have a diffractive power, as illustrated by the IOL 18 shown in FIG. 1B. The diffractive power can, for example, comprise positive or negative add power, and that add power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens directs incoming light into a number of diffraction orders. As light 13 enters from the front of the eye, the multifocal lens 18 directs light 13 to form a far field focus 15a on retina 16 for viewing distant objects and a near field focus 15b for viewing objects close to the eye. Depending on the distance from the source of light 13, the focus on retina 16 may be the near field focus 15b instead. Typically, far field focus 15a is associated with $0^{th}$ diffractive order and near field focus 15b is associated with the $1^{st}$ diffractive order, although other orders may be used as well.

Multifocal ophthalmic lens 18 typically distributes the majority of light energy into the two viewing orders, often with the goal of splitting imaging light energy about evenly (50%:50%), one viewing order corresponding to far vision and one viewing order corresponding to near vision, although typically, some fraction goes to non-viewing orders.

Figure 2A:
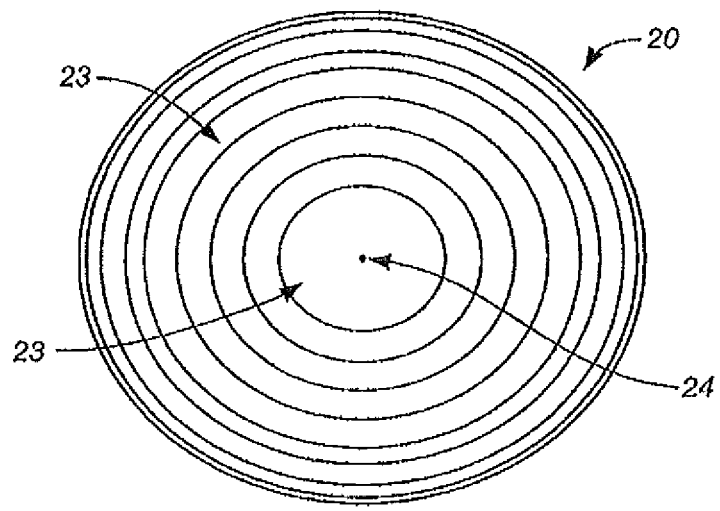
FIG. 2A is a front view of a diffractive multifocal ophthalmic lens.
Figure 2B:
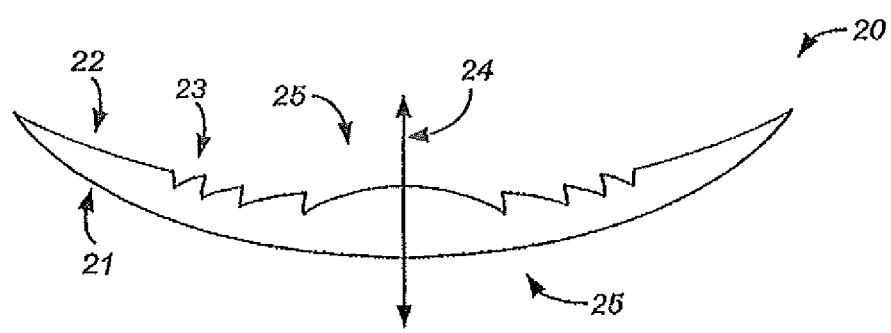
FIG. 2B is a cross-sectional view of the lens of FIG. 2A.

In some embodiments, corrective optics may be provided by phakic IOLs, which can be used to treat patients while leaving the natural lens in place. Phakic IOLs may be angle supported, iris supported, or sulcus supported. The phakic IOL can be placed over the natural crystalline lens or piggy-backed over another IOL. It is also envisioned that the present invention may be applied to inlays, onlays, accommodating IOLs, spectacles, and even laser vision correction FIGS. 2A and 2B show aspects of a standard diffractive multifocal lens 20. Multifocal lens 20 may have certain optical properties that are generally similar to those of multifocal IOL 18 described above. Multifocal lens 20 has an anterior lens face 21 and a posterior lens face 22 disposed about optical axis 24. The faces 21, 22 of lens 20 typically define a clear aperture 25. As used herein, the term "clear aperture" means the opening of a lens or optic that restricts the extent of a bundle of light rays from a distant source that can be imaged or focused by the lens or optic. The clear aperture is usually circular and is specified by its diameter, and is sometimes equal to the full diameter of the optic.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a plurality of annular optical zones or echelettes 23 spaced about optical axis 24. While analytical optics theory generally assumes an infinite number of echelettes, a standard multifocal diffractive IOL typically has at least 9 echelettes, and may have over 30 echelettes. For the sake of clarity, FIG. 2B shows only 4 echelettes. Typically, an IOL is biconvex, or possibly plano-convex, or convex-concave, although an IOL could be plano-plano or other refractive surface combinations.

Figure 3A:
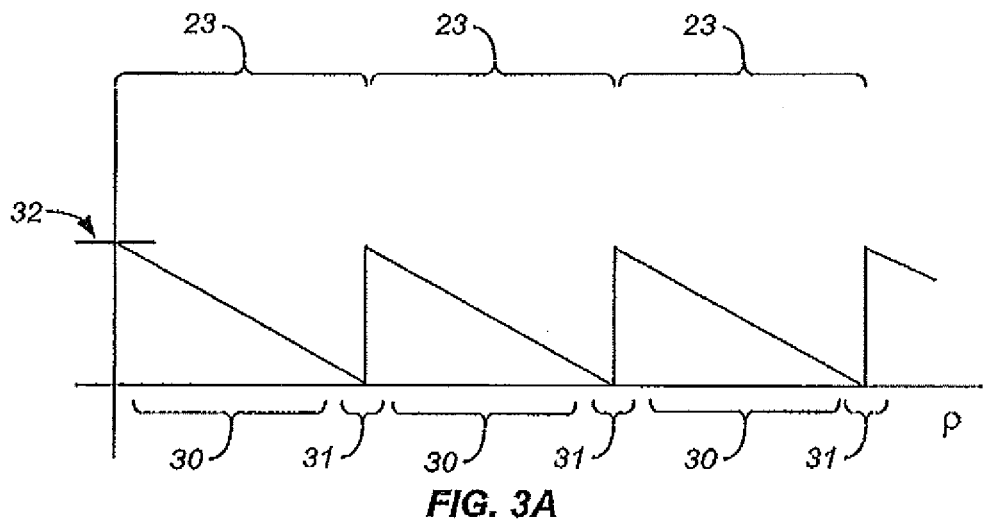
FIGS. 3A-3B are graphical representations of a portion of the diffractive profile of a conventional diffractive multifocal lens.
Figure 3B:
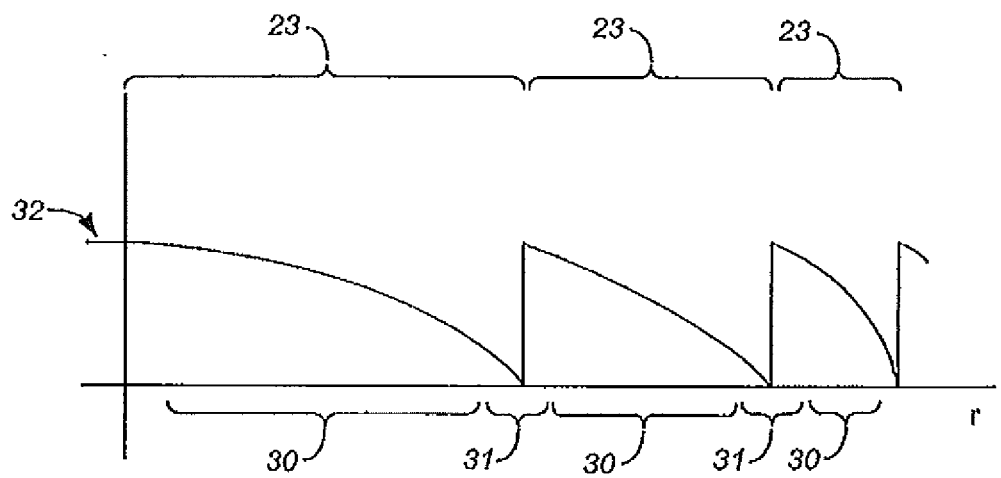

FIGS. 3A and 3B are graphical representations of a portion of a typical diffractive profile of a multifocal lens. While the graph shows only 3 full echelettes, typical diffractive lenses extend to at least 9 echelettes to over 32 echelettes. In FIG. 3A, the height of the surface relief profile (from a plane perpendicular to the light rays) of each point on the echelette surface is plotted against the square of the radial distance ($r^2$ or $\rho$) from the optical axis of the lens. In multifocal lenses, each echelette 23 may have a diameter or distance from the optical axis which is often proportional to $\sqrt{n}$, n being the number of the echelette 23 as counted from optical axis 24. Each echelette has a characteristic optical zone 30 and transition zone 31. Optical zone 30 typically has a shape or downward slope that may be linear when plotted against $\rho$ as shown in FIG. 3A. When plotted against radius r, optical zone 30 has a shape or downward slope that is parabolic as shown in FIG. 3B. As for the typical diffractive multifocal lens, as shown here, all echelettes have the same surface area. The area of echelettes 23 determines the add power of lens 20, and, as area and radii are correlated, the add power is also related to the radii of the echelettes.

As shown in FIGS. 3A and 3B, transition zone 31 between adjacent echelettes is sharp and discontinuous. The height of the lens face sharply transitions from sloping steadily downwards to stepping vertically upwards, and the transitions abruptly back to sloping steadily downwards again. In doing so, echelettes 23 also have a characteristic step height 32 defined by the distance between the lowest point and height point of the echelette. Hence, the slope (or first derivative) and/or the curvature (second derivative) of the diffractive surface are discontinuous adjacent the transitions.

Finite Microstructure

Figure 4:
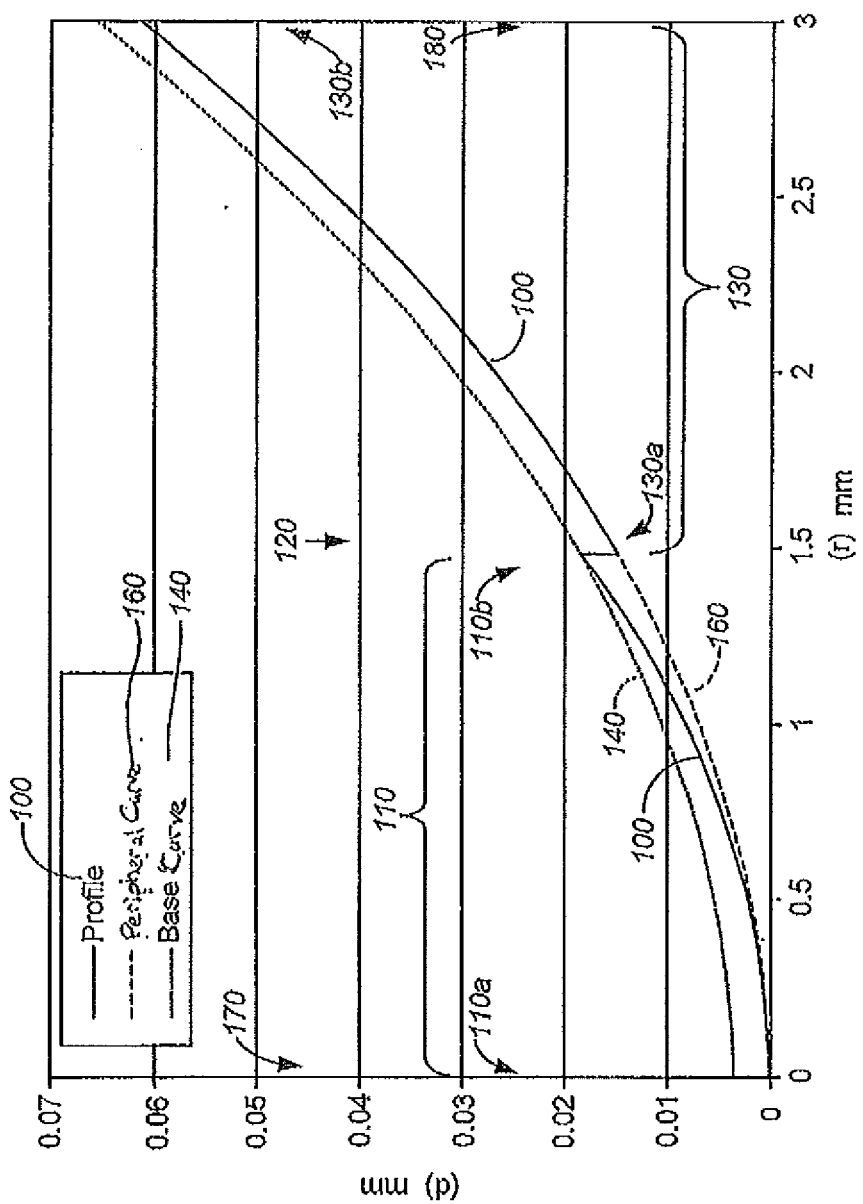
FIG. 4 shows aspects of a single microstructure lens according to embodiments of the present invention.
Figure 4:
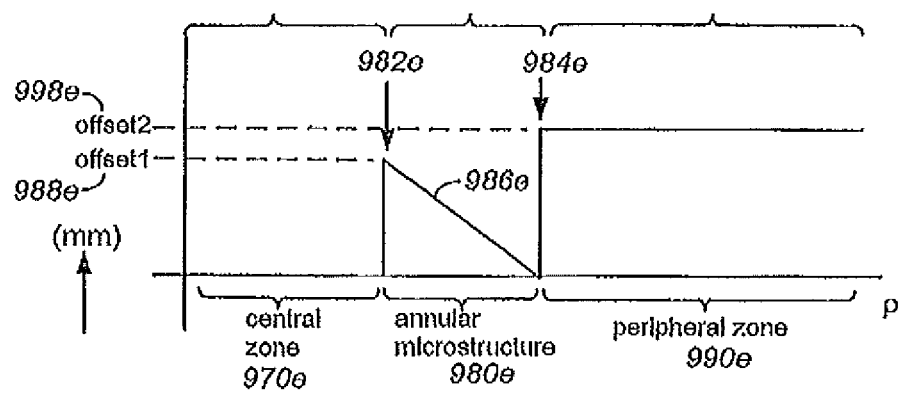

FIG. 4 provides a graphical representation of a cross section of a single microstructure lens profile 100, according to embodiments of the present invention. Only half of the lens is shown, although since the lens is rotationally symmetric, the other half is a mirror image that complements the lens at the left side of FIG. 4. Profile 100 of the single ring surface includes an inner portion or single ring 110, a step or transition 120, and an outer portion 130. Inner portion 110 extends between a central location 170 of profile 100 and transition 120, and outer portion 130 extends between transition 120 and a peripheral location 180 of profile 100. Central location 170 is typically disposed at the optical axis (although in certain embodiments it may be offset—for example to match the pupil center or an offset eye axis, etc.). In this specific example, transition 120 is disposed at a distance of about 1.5 mm from the optical axis, and peripheral location 180 is disposed at the diameter of the clear aperture of the lens, here at a distance of about 3.0 mm from the optical axis. In some cases, transition 120 can be disposed at a distance from the optical axis that is within a range from about 0.5 mm to about 2.0 mm, and peripheral location 180 can be disposed at a distance from the optical axis that is within a range from about 2.0 to about 3.5 mm, or bigger (for example, for contact lenses, the ranges would be approximately 15% larger due to the optically more powerful position of contact lens compared to an IOL; those skilled in the art would appropriately scale certain dimensions depending on the application).

As shown in FIG. 4, the surface height or sag (d) from a reference plane perpendicular to the optical axis, of each point on the lens profile is plotted against the radial distance (r) from the optical axis of the lens. As shown here, the value of displacement or total sag (d) can have a value within a range from about 0 mm to about 0.07 mm. The total sag can depend on the refractive shape of the surface and can have a value, for an IOL, of typically between 0 mm and about 2 mm, or to about minus 2 mm, in cases where the surface is concave.

Inner Portion

Inner portion or echelette 110 includes a center 110a and a peripheral edge 110b. At center or central section 110a of inner portion 110, the sag (d) of inner portion 110 is substantially equivalent to the displacement or sag (d) of peripheral curve 160. At peripheral edge 110b, the sag (d) of inner portion 110 is substantially equivalent to the sag (d) of diffractive base curve 140. Where radial distance (r) is zero, sag (d) of inner portion 110 is equivalent to the value of the peripheral curve 160. The value of sag (d) between radial distance zero and radial distance at the peripheral edge 110b, for example at 1.5 mm, gradually and smoothly changes from the value of peripheral curve 160 (at r=0) to diffractive base curve 140 (at r=1.5 mm) in a parabolic fashion. As shown here, inner portion 110 can present a parabolic shape, for example as described in Equation 4a of Cohen, Applied Optics, 31:19, pp. 3750-3754 (1992), incorporated herein by reference. It is understood that in some instances, inner portion 110 may present any of a variety of shapes or profiles, including hyperbolic shapes, spherical shapes, aspheric, and sinusoidal shapes. The shape of inner portion 110 can be imposed on a refractive shape.

Transition

At the peripheral edge 110b, where the radial distance (r) is 1.5 mm, the value of sag (d) steps or changes from the value of diffractive base curve 140 to the value of peripheral curve 160. Where radial distance (r) corresponds to transition 120, sag (d) of inner portion 110 is equivalent to the value of the diffractive base curve 140. Relatedly, the displacement of the profile 100 approaches that of the peripheral curve 160 as the radial distance increases from a value of zero to a value of about 1.5 mm. The value of the offset can be determined along the vertical axis. The offset value may be selected depending on the amount of phase delay. According to one embodiment, the inner portion 110 and the outer portion 130 may not end up at the same vertical height at position 110b/130a. One way to connect these two endpoints is by using a straight vertical line. As shown here, the diffractive transition step provides a sharp step in the profile. In some cases the transition is characterized by a step height having a value within a range from about 0.5 µm and about 4 µm. According to some embodiments, a transition can be characterized by a step height having a value within a range of about 1.5 µm and 2.5 µm.

Outer Portion

Outer portion 130 includes an inner or central edge 130a and a peripheral edge 130b. At inner edge 130a, the sag (d) of outer portion 130 is substantially equivalent to the sag (d) of peripheral curve 160. At peripheral edge 130b, the sag (d) of outer portion 130 remains substantially equivalent to the sag (d) of peripheral curve 160. The value of sag (d) for the outer portion 130 of profile 100 between radial distance 1.5 mm and radial distance 3.0 mm is equivalent to the value of peripheral curve 160. The sag of the profile 100 and the peripheral curve 160 are approximately equivalent between radial distance values of 1.5 mm and 3.0 mm. As shown here, outer portion 130 can provide a normal spherical or aspherical curve, such as a Tecnis aspheric surface, which corrects or treats the ocular spherical aberration. For a more detailed description of the Tecnis IOL see U.S. Pat. No. 7,615,073, the content of which is incorporated herein by reference. Virtually any aspheric profile may be used. In some cases, a Tecnis profile, or an aspherical surface that modifies, reduces, or increases the ocular spherical aberration, can be used. A refractive multifocal surface can also be used, or a refractive aspherical or zonal refractive surface that extends the depth of focus. The diffractive multifocal may be on the opposite side.

As compared with lenses having a plurality of echelettes, and where step height increases or decreases as radial distance increases, embodiments of the present invention encompass lens configurations where such step configurations are absent.

The size of the human pupil varies with illumination. In bright light the pupil is small, and in dim or low light conditions the pupil is large. In addition, the size of the human pupil varies with accommodative effort. Without accommodative effort, the pupil is larger than with accommodative effort. Hence, for a smaller pupil, it may be desirable to provide a design that places a relative emphasis on intermediate or near vision. For a larger pupil, it may be desirable to provide a design that places a relative emphasis on far vision. Such considerations may affect IOL design.

The condition of dysphotopsia (e.g. halos) that is present for multifocal lenses is observed to be dominated by separation of two foci. Accordingly, pursuant to exemplary embodiments of the present invention, the lens may include only a single microstructure ring, so that light separation between distinct foci is not complete, as compared to diffractive multifocal IOLs having multiple echelettes.

In typical reading or near vision conditions where the light is bright, the size of the pupil is small, e.g. between about 1 mm and 2 mm in diameter, and the eye has a large depth of focus (for example from a pinhole effect), almost irrespective of the optics of the IOL. Large pupil size, e.g. larger than about 4-5 mm in diameter, generally applies to low light conditions, and is often associated with distance vision for which the power of the IOL is typically established. Therefore, many patients would benefit most from an IOL that enhances the depth of focus in order to view at intermediate distances. An IOL having a single echelette or ring effectively increases the depth of focus for intermediate pupil sizes, while maintaining the general increased depth of focus of small pupil sizes, and also maintaining an emphasis on far vision for large pupil sizes. At the same time, since the single echelette and the remaining surface area of the optic or remaining lens portion ("non-echelette") have unequal surface areas for almost all pupil sizes, there is an incomplete split between the foci. Since the split of light is incomplete, the separation of foci is incomplete. This incomplete separation of foci contributes to the extended depth of focus and the attenuation of dysphotopsia (e.g. halos).

FIG. 4A provides a graphical representation of a portion of a lens diffractive profile according to embodiments of the present invention, which further explains a single microstructure embodiment. In FIG. 4A, the height of the surface relief profile (from a plane perpendicular to the light rays) of each point on the echelette surface is plotted against the square of the radial distance ($r^2$ or $\rho$) from the optical axis of the lens. The echelette can have a characteristic optical zone 930 and transition zone 931. Optical zone 930 can have a shape or downward slope that may be linear when plotted against $\rho$ as shown in FIG. 4A. When plotted against radius r, optical zone 930 can have a shape or downward slope that is parabolic. As depicted here, central optical zone 930 can provide a central parabolic echelette. An outer (refractive) zone can follow the base radius with a fixed offset. In some cases, the profile can present an echelette or central portion 923a and a refractive zone or peripheral portion 923b.

As shown in FIG. 4A, transition zone 931 between the optical zone 930 and the outer zone 933 can be sharp and discontinuous. Similarly, a vertical transition between central portion or echelette 923a and peripheral portion or refractive zone 923b can be sharp and discontinuous. The height of the lens face sharply transitions from sloping steadily downwards (e.g. across optical zone 930) to stepping vertically upwards (e.g. at transition zone 931), and the transitions abruptly back to sloping steadily or substantially horizontal. In doing so, echelette 923a or optical zone 930 also has a characteristic step height 932 defined by the distance between the lowest point and highest point of the echelette. Hence, the slope (or first derivative) and/or the curvature (second derivative) of the diffractive surface are discontinuous adjacent the transition. The first derivative can be indicated by the direction of the lines, and the second derivative can be indicated by the curve of the line.

According to some embodiments, light comes from below, in the direction indicated by arrow A, and only hits the echelette 930 of the profile. According to some embodiments, in theoretical terms light does not hit the vertical connection of the optical zone, and hence the profile can be said to have no transition zone. According to some embodiments, in practice when one attempts to produce such a profile, for instance by lathe cutting, it may be difficult to reproduce the sharp corner (e.g. at where the optical zone connects with the adjacent optical zone) and hence the corner may be rounded to some extent due to the finite chisel radius. Such rounding may have a negligible effect on the optical performance. According to related embodiments, transition zone 931, which can be referred to as the transition from the echelette to the adjacent zone or zones, can be shaped in a specific way, so as to optimize the optical performance, for example, to minimize scatter from a sharp transition.

According to some embodiments, a central portion 923a can be defined as an echelette, and a peripheral portion 923b can be defined as a refractive zone.

FIG. 4B is a graphical representation of a diffractive profile 971 of a lens, plotting the height of the surface relief profile at a particular point of an echelette 972 versus ρ, the square of the radius or distance displaced from a plane perpendicular to the light rays, and shown with a conventional diffractive profile 975, shown by the dotted line. According to some embodiments, an echelette can include an optical zone or primary zone 977 and a transition zone 976. According to some embodiments, a central portion 972a can be defined as an echelette, and a peripheral portion 972b can be defined as a refractive zone. According to some embodiments, an echelette includes one primary zone and one transition zone.

As shown in FIG. 4B, transition zone 976 between the echelette and the adjacent zone 978 may not be sharp and discontinuous. The height of the lens face can smoothly transition. In addition, echelette 972, or central portion 972a, can have a characteristic profile height 974, and peripheral portion 972b can have a characteristic profile height 974a defined by the distance between the lowest point and height point of the echelette or portion. Hence FIG. 4B illustrates that the central echelette may be of another shape, that there may be a transition zone, that the phase offset (height) at 974a may be different from the phase offset (height) of the central zone 974, and that the outer or peripheral zone may have an alternative aspherical shape.

FIG. 4C is a graphical representation of a lens profiles, according to embodiments of the present invention disclosing a single echelette surrounding a central refractive zone of the lens. The lens profile embodiment in FIG. 4C has one single echelette or microstructure 980e, which is positioned as an annulus around a central refractive optical zone 970e. The annular echelette has an inner radius 982e and an outer radius 984e, a profile shape 986e and a profile height 988e (offset1). The annular echelette 980e may be surrounded by a refractive peripheral zone 990e, having a profile height 998e (offset2). Profile heights 988e, 998e may be characterized by their respective distances from the base/central refractive zone. While it is not shown in FIG. 4C, it is noted that the refractive central and peripheral zones can be aspherical surfaces, designed to modify ocular aberrations, e.g. spherical aberration. A transition (e.g. vertical line) between a microstructure and a refractive zone, as displayed in FIG. 4E may be sharp or smooth, as further described elsewhere herein. In addition, the refractive zones may be spherical or aspherical, or mixed, having a spherical refractive zone and an aspherical refractive zone.

Figure 4D:
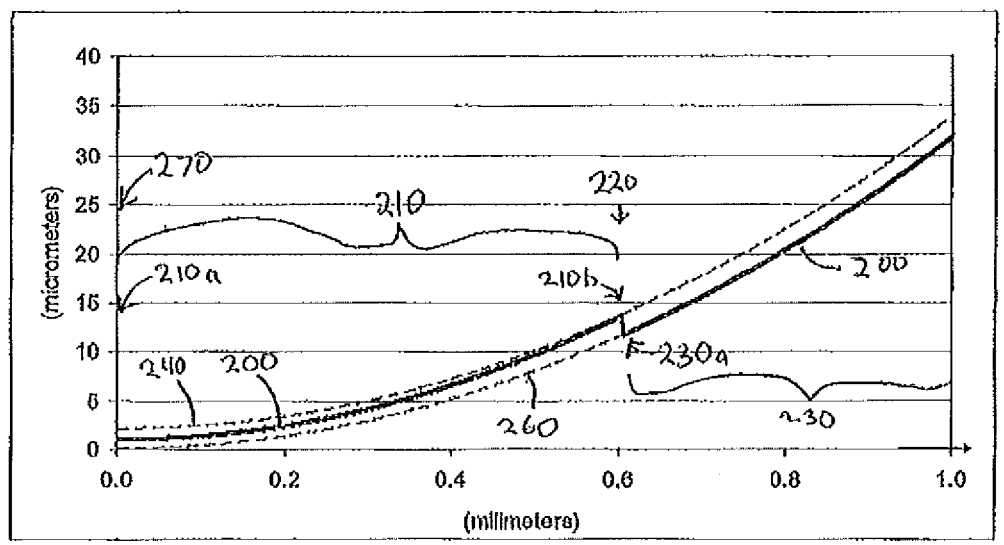
FIG. 4D shows aspects of a single microstructure lens according to embodiments of the present invention.

FIG. 4D provides a graphical representation of a cross section of a single microstructure lens profile 200 on the posterior surface of a lens with a ring diameter of 1.21 mm and a stepheight at 220 of 2.05 μm, corresponding with a phase delay of 0.5 lambda (see table 2). In this example, the ring diameter was reduced from 1.5 mm (which is the inner ring diameter for a 2.0 Diopter conventional IOL diffractive lens) to 1.21 mm by a scaling factor √2, as described in U.S. Pat. No. 5,121,980 (Cohen). Only the inner portion and part of the outer portion of half of the lens is shown, although since the lens is rotationally symmetric, the other half is a mirror image. Profile 200 of the single ring surface includes an inner portion 210 or single ring, a step or transition 220, and an outer portion 230. The outer portion 230 extends beyond that disclosed in FIG. 4D to 2.5 mm. Inner portion 210 extends between a central location 270 of profile 200 and transition 220. Outer portion 230 extends between transition 220 and a peripheral location (not shown).

The inner portion or echelette 210 includes a center 210a and a peripheral edge 210b. At center or central section 210a of inner portion 210 where radial distance is zero, the sag (d) of inner portion is between the sag (d) of the diffractive base curve 240 and the sag (d) of the peripheral curve 260 at 1.03 μm from the peripheral curve 260, corresponding with a phase delay of 0.25 lambda (see table 2). At peripheral edge 210b, the sag (d) of inner portion 210 is substantially equivalent to the sag (d) of diffractive base curve 240 at 13.8 μm. The value of sag (d) between radial distance zero and radial distance at the peripheral edge 210b at 0.61 mm, gradually and smoothly changes from 1.03 μm (at r=0) to the value of the base curve 240 (at r=0.61 mm) which is 13.8 μm. This change occurs in a parabolic fashion. As shown here, inner portion can present a parabolic shape, for example as described in Equation 4a of Cohen, Applied Optics, 31:19, pp. 3750-3754 (1992), incorporated herein by reference.

At the peripheral edge 210b where the radial distance (r) is 0.61 mm, the value of sag (d) steps or changes from the value of diffractive base curve 240 to the value of peripheral curve 260. Where radial distance (r) corresponds to transition 220, sag (d) of inner portion is equivalent to the value of the diffractive base curve 240. Relatedly, the displacement of the profile approaches that of the diffractive base curve as the radial distance increases from a value of zero to a value of about 0.61 mm. The stepheight is 2.05 μm resulting in a phase delay of 0.5.

The outer portion 230 includes an inner or central edge 230a and a peripheral edge (not shown). At inner edge 230a, the sag (d) of outer portion is substantially equivalent to the sag (d) of peripheral curve 260. At peripheral edge, the sag (d) of outer portion remains substantially equivalent to the sag (d) of peripheral curve 260. The value of sag (d) for the outer portion of profile between radial distance 0.61 mm and the peripheral portion at radial distance 2.5 mm is equivalent to the value of peripheral curve 260. The sag of the profile and the peripheral curve 260 are approximately equivalent between radial distance values of 0.61 mm and 2.5 mm. Outer portion can provide a normal spherical or aspherical curve, such as a Tecnis aspheric surface, which corrects or treats the ocular spherical aberration.

Profile Parameters

The profile design can be characterized in terms of a set of parameters. Conventional multifocal lenses, having a plurality of echelettes, are typically characterized by the parameters: add power and light distribution. For example, the single echelette of a profile can be described as reflecting a lens add power and a light distribution (as discussed in more detail below). As discussed in previously incorporated U.S. patent application Ser. No. 61/047,699 and Ser. No. 12/109,251, both filed Apr. 24, 2008, lens add power can be based on the diameter or radial position or location of a profile echelette, and light distribution can be based on the relative height of an echelette.

Diffractive Power and Geometry of the Echelette

In conventional diffractive IOLs, the diameter (or size or width or surface area) of the echelette is related to the diffractive power of the lens. As such, variations of the geometry of the single echelette design disclosed herein have been characterized according to conventional diffractive IOL design in terms of add power. In particular, the radius of the single echelette embodiments disclosed herein, are equivalent to the inner radius of conventional diffractive IOLs with the same add power. As one skilled in the art knows, the add power would not necessarily describe the optical characteristics of the single echelette embodiments disclosed herein. According to some embodiments, the diffractive power of the lens has a value within a range from about 0.5 diopters to about 3.0 diopters representing the echelette radius and diameter as detailed in Table 1 below. Table 1 provides dimensions of various samples, where D represents the power in diopters, R represents the radius of the ring, or echelette, in mm, and De represents the diameter of the ring in millimeters. In alternative embodiments, the single echelette is an annulus around, or within, a refractive surface. In such case, a translation between diffractive power and echelette size is represented by the surface area of the echelette. Table 1 provides dimensions for surface areas of the echelette.

TABLE 1

| D | R (mm) | De (mm) | Area (mm²) |
|---|---|---|---|
| 0.5 | 1.48 | 3 | 6.9 |
| 1 | 1.05 | 2.1 | 3.5 |
| 1.5 | 0.86 | 1.7 | 2.3 |
| 2 | 0.74 | 1.5 | 1.7 |
| 2.5 | 0.66 | 1.3 | 1.4 |
| 3 | 0.61 | 1.2 | 1.2 |

Phase Delay and Geometry of the Echelette

The step height or profile height can determine the phase delay or phase shifting profile. A greater step height can correspond to a greater phase shift. In conventional diffractive IOLs, the phase shift is related to the light distribution of the lens. As such, variations of the geometry of the single echelette design disclosed herein have been characterized according to conventional diffractive IOL design in terms of light distribution. As one skilled in the art knows, the light distribution would not necessarily describe the optical characteristics of the single echelette embodiments disclosed herein. According to some embodiments, a lens can include a transition characterized by a step height producing a phase shift between about 0.25 and about 1 times the design wavelength. In some cases, a diffractive profile can be characterized by a design wavelength, and the lens can include a transition characterized by a step height producing a phase shift between about 0.15 and about 2 times the design wavelength. According to some embodiments the lens may include a transition characterized by a step height producing a phase shift of about 0.5. In other embodiments, the lens may include a transition characterized by a step height of about 0.4.

In terms of an echelette transition, the sag at the transition increases an amount equal to the offset value. Table 2 below provides dimensions of various samples disclosing the relationship between phase delay (in wavelengths) and step height (in µm), as valid for an example IOL material.

TABLE 2

| Phase Delay | Stepheight |
|---|---|
| 0.896 | 3.68 |
| 0.700 | 2.87 |
| 0.590 | 2.42 |
| 0.509 | 2.09 |
| 0.500 | 2.05 |
| 0.423 | 1.74 |
| 0.366 | 1.50 |
| 0.350 | 1.44 |
| 0.250 | 1.03 |
| 0.150 | 0.62 |

Thus, in an exemplary embodiment where the lens has a power of 2.5 D with a 0.423 phase shift according to the design disclosed in FIG. 4, the radius of the single ring would be 0.66 mm and the stepheight would be 1.74 µm.

Pupil Dependence

In an exemplary embodiment, the single ring central or single central echelette design has an optical performance that depends on the pupil size. For very small pupils, where the pupil is smaller than the size of the central echelette, the echelette will act as a refractive lens, having a very large depth of focus, due to the pinhole effect. For higher and medium pupil sizes, where the pupil covers the central echelette and a part of the outer zone, the lens will act as a diffractive/refractive lens, with an appropriate phase shift. The size of the central echelette influences the pupil dependence of the lens. As such, the size of the central echelette can be chosen, depending on the pupil sizes of a specific patient. For example, the pupil sizes of a patient may be measured in bright light, in dim light, during far vision and during near vision, and in the different combinations of light level and accommodative effort. These different pupil sizes, which may be defined as pupil dynamics, can be used as input parameters for an optimal design of the single ring or single echelette design.

For example, if a patient has a pupil diameter during near vision (e.g. viewing target at close distance, with high accommodative effort) smaller than 2 mm, having this pupil dimension with both bright and dim light, then the size of the central echelette may be selected to be smaller than 2 mm (e.g. outer diameter of the circular echelette of FIG. 4A), as to provide adequate near and/or intermediate vision. Relatedly, if a patient has a pupil diameter during near vision larger than 2 mm, having this pupil dimension with both bright and dim light, then the size of the central echelette may chosen 2 mm or larger, as to provide adequate near and intermediate vision. In general, the diameter of the central echelette can be smaller than the smallest pupil size the patient has under any condition (e.g. bright/dim light; near/far vision). For any type of pupil dynamics, the size, the profile, and the offsets may be chosen to maximize the lens performance for that specific patient, or group of patients. Generally, this is a trade off between the different vision circumstances (combinations of light level and accommodative effort) at which the pupil of the patient is measured. Accordingly, exemplary embodiments include a method of designing an ophthalmic lens comprised of utilizing pupil size measurements and based on the measurements determining the size of an isolated echelette to impose on the surface of a lens. The pupil size measurements may be based on a group of patients.

Evaluation of Variations of a Specific Example

With regard to the example as shown in FIG. 4A, a number of variations have been analyzed. In these examples, the central echelette has been varied in size, and step height (offset). As such, variations of the echelette design have been characterized according to conventional diffractive IOL design in terms xD/y %, where xD represents the add power that the echelette design represents (e.g. based on echelette size and/or position, and step height), and y % represents the portion of the light directed into the first order focus. The add power and light distribution are being used herein to characterize the geometry of the central echelette. In particular, the radius of the single echelette embodiments disclosed herein, are equivalent to the inner radius of conventional diffractive IOLs with the same add power. Analogously, the step height and associated phase delay of the single echelette embodiments disclosed herein are equivalent to the step height/phase delay of conventional diffractive IOLs with the same light distribution. As one skilled in the art knows, the add power and light distribution would not describe the optical characteristics of the single echelette embodiments as disclosed herein. Table 3 discloses the relationship between percentage of light between near and far focus, phase delay, and stepheight for the IOL material in the example.

TABLE 3

| Percent Near | Phase Delay | Stepheight |
|---|---|---|
| 99 | 0.896 | 3.68 |
| 85 | 0.700 | 2.87 |
| 68 | 0.590 | 2.42 |
| 52 | 0.509 | 2.09 |
| 50 | 0.500 | 2.05 |
| 35% | 0.423 | 1.74 |
| 25 | 0.366 | 1.50 |
| 23 | 0.350 | 1.44 |
| 10 | 0.250 | 1.03 |
| 3 | 0.150 | 0.62 |

For example, a 2D/35% echelette design represents a lens with a central echelette with a radius of 0.74, wherein the phase delay is 0.423 and the stepheight is 1.74. Similar nomenclature is used in conjunction with the designs as analyzed in FIGS. 6-20 herein.

Figure 5:
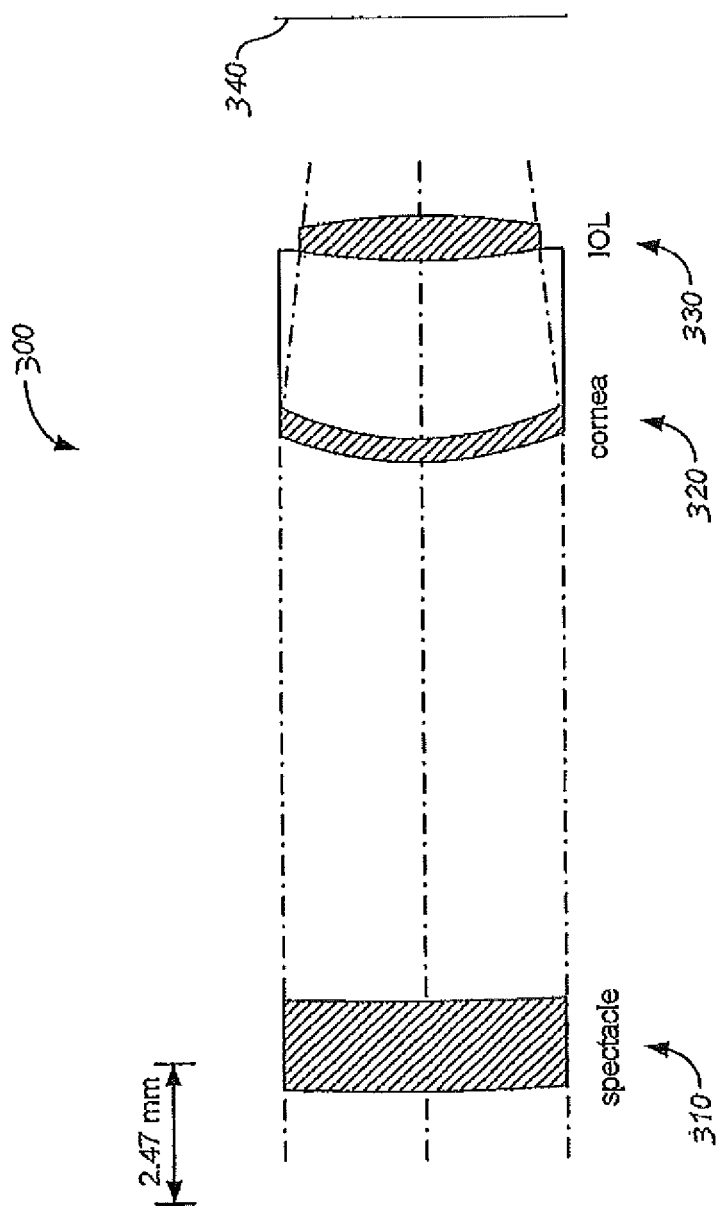
FIG. 5 illustrates aspects of an optical system layout of a schematic eye according to embodiments of the present invention.

FIG. 5 illustrates an optical system layout 300 of a schematic eye that includes a spectacle lens 310, a cornea 320, an intraocular lens 330, and a retina 340. The cornea 320 has the spherical aberration of an average cataract patient. The schematic eye also has the average chromatic aberration of the human eye. This so called ACE model, or average cornea eye model, is based on actual wavefront measurements collected from a sampling of cataract patients, and chromatic aberration and dispersion of the human eye. The eye model is substantially described in: Norrby, S., Piers, P., Campbell, C., & van der Mooren, M. (2007) Model eyes for evaluation of intraocular lenses. Appl Opt, 46 (26), 6595-6605, the content of which is incorporated herein by reference. Using the ACE model, it is possible to evaluate various lens profiles. By changing the power of the spectacle lens, it is possible to generate various defocus curves. For example, a negative power spectacle lens can mimic the effect of looking at an object at a close distance.

With regard to the example as shown in FIG. 4A, a number of variations have been analyzed, and the image quality versus defocus has been calculated in the ACE eye model. In order to present information about pupil dependent performance of the example designs, the image analysis is carried out for pupil diameters of 2.0 mm, 3.0 mm, and 4.0 mm. This is depicted in FIGS. 6A to 9D, and FIGS. 10A to 13C. Hence, FIGS. 6A to 9D and FIGS. 10A to 13C can be considered as a single set. In this series, the size of the echelette is being varied from 1.2 mm to 3.0 mm in diameter, and the step height is being varied from 0.6 to 3.7 µm. The echelette geometry in this series is characterized in terms xD/y %. The general lens configuration was an equi-biconvex optic, having an aspherical anterior surface and a spherical posterior surface. The single ring design was applied onto the posterior surface.

Figure 5A:
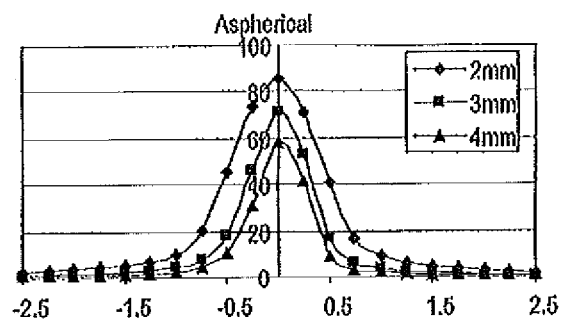
FIGS. 5A-5C show aspects of reference designs according to embodiments of the present invention.
Figure 5B:
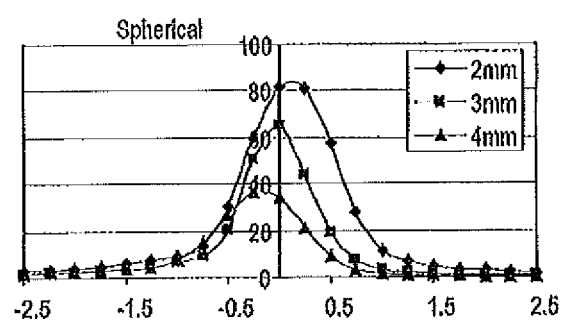
Figure 5C:
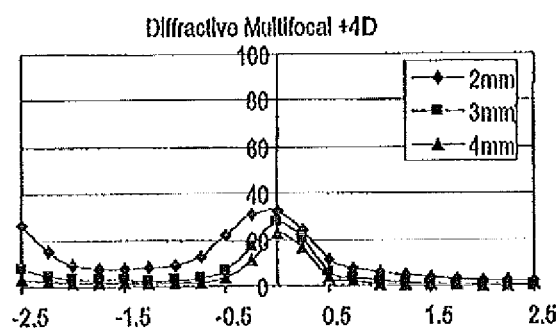
Figure 6A:
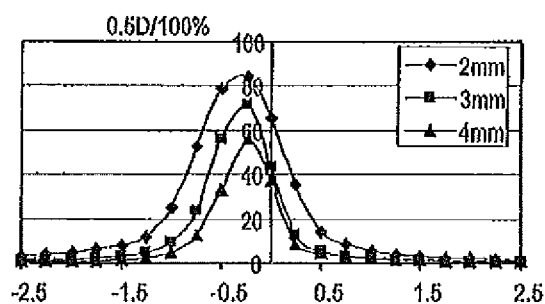
FIGS. 6A-6D illustrate aspects of design profile evaluation according to embodiments of the present invention.
Figure 6B:
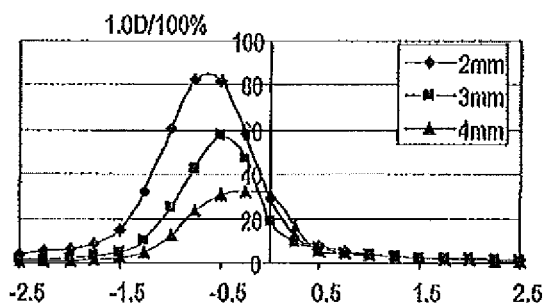
Figure 6C:
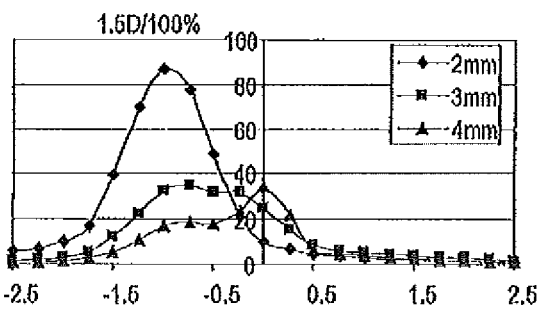
Figure 6D:
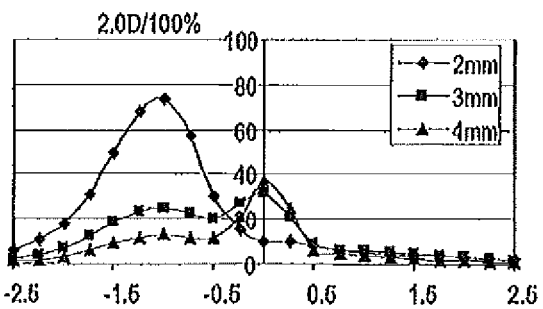
Figure 7A:
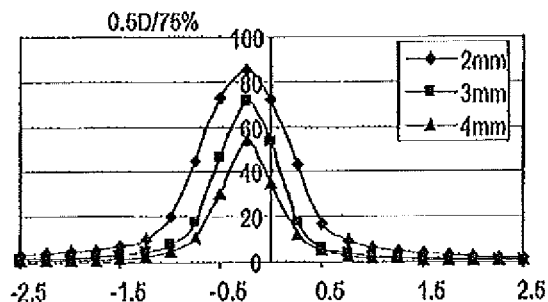
FIGS. 7A-7D illustrate aspects of design profile evaluation according to embodiments of the present invention.
Figure 7B:
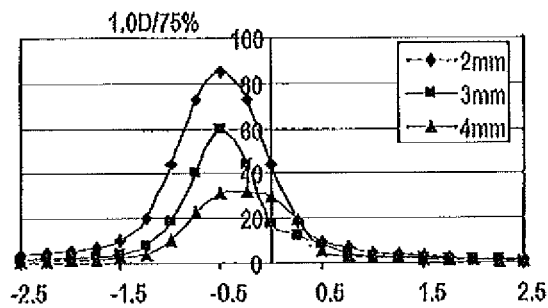
Figure 7C:
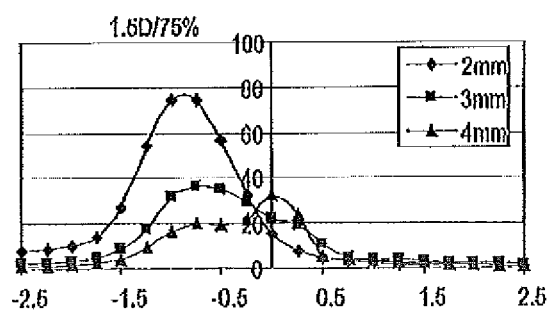
Figure 7D:
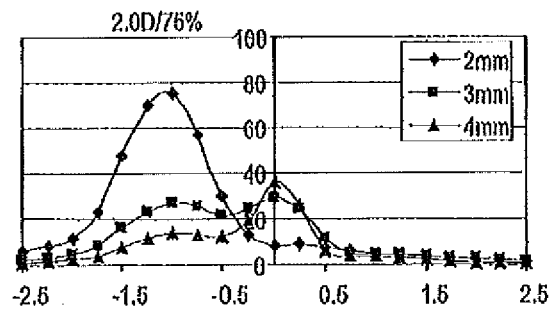
Figure 8A:
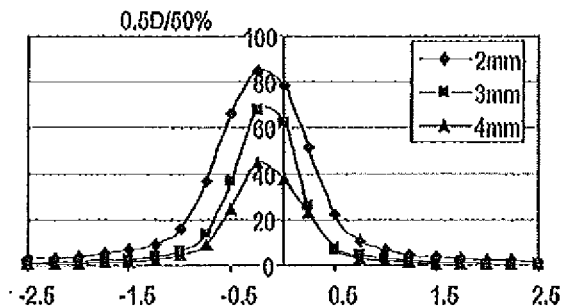
FIGS. 8A-8D illustrate aspects of design profile evaluation according to embodiments of the present invention.
Figure 8B:
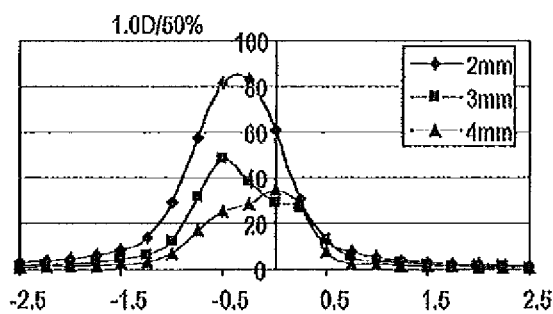
Figure 8C:
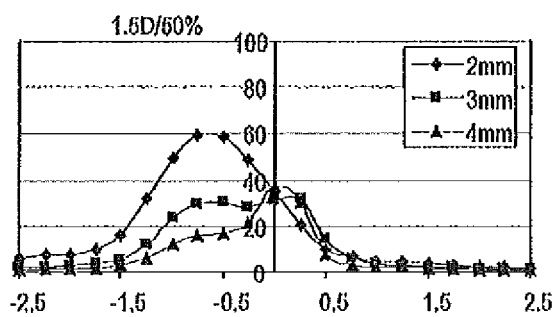
Figure 8D:
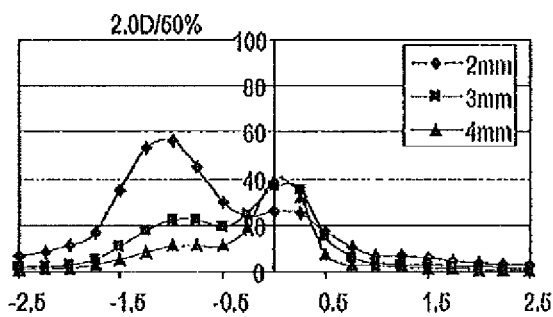
Figure 9A:
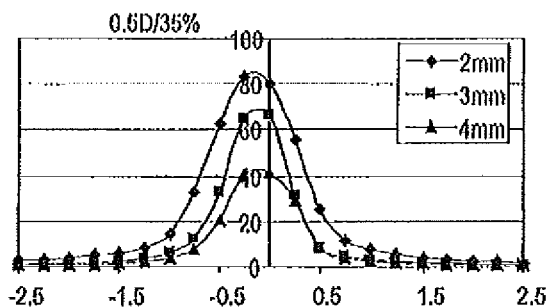
FIGS. 9A-9D illustrate aspects of design profile evaluation according to embodiments of the present invention.
Figure 9B:
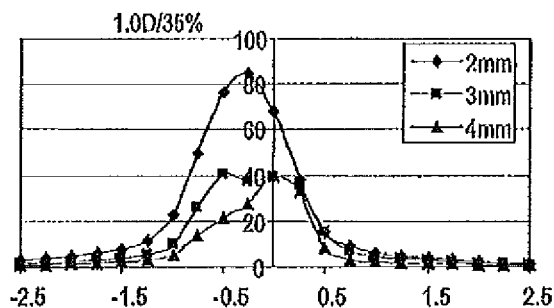
Figure 9C:
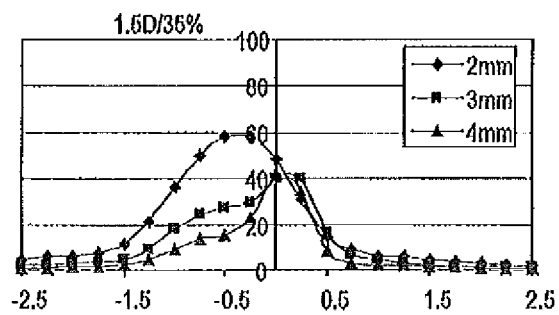
Figure 9D:
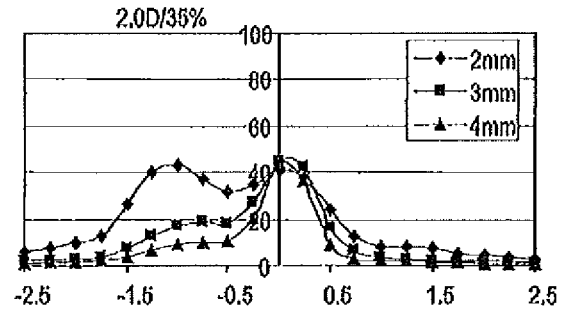
Figure 10A:
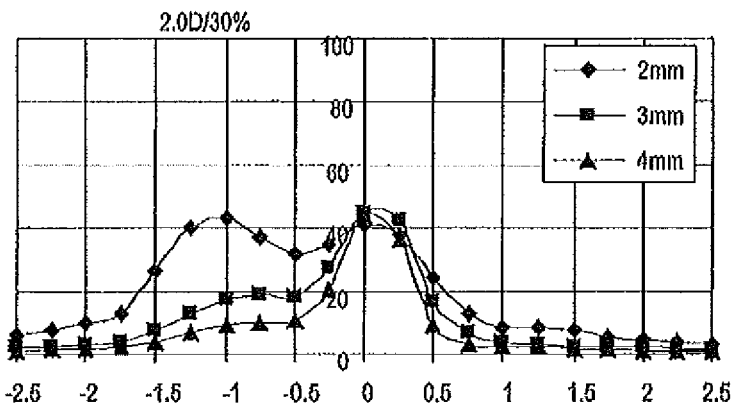
FIGS. 10A-10C illustrate aspects of design profile evaluation according to embodiments of the present invention.
Figure 10B:
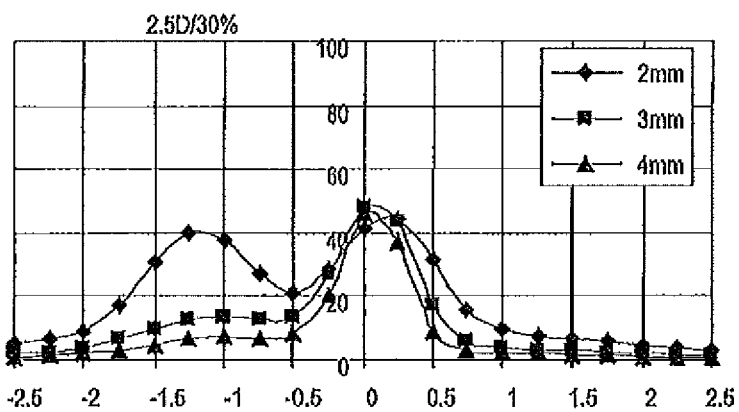
Figure 10C:
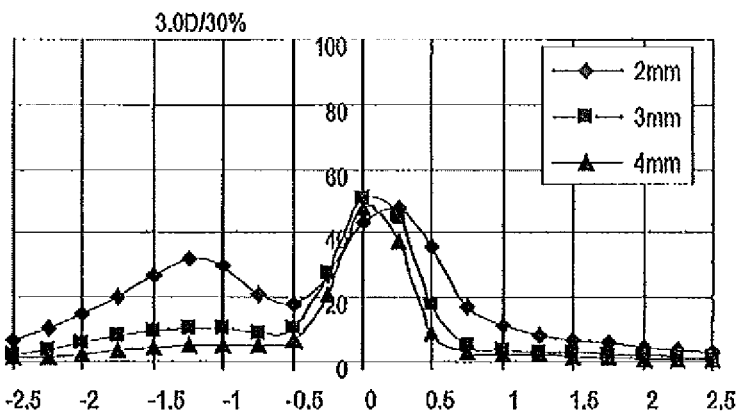
Figure 11A:
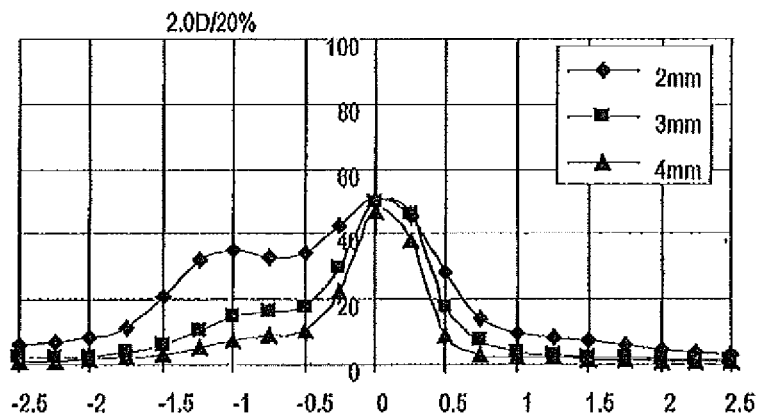
FIGS. 11A-11C illustrate aspects of design profile evaluation according to embodiments of the present invention.
Figure 11B:
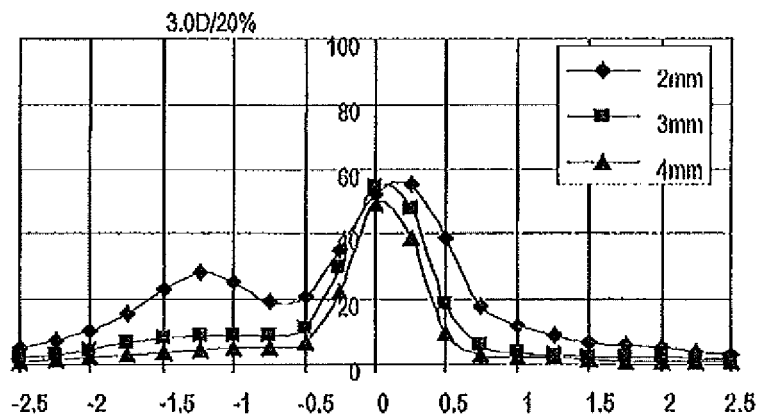
Figure 11C:
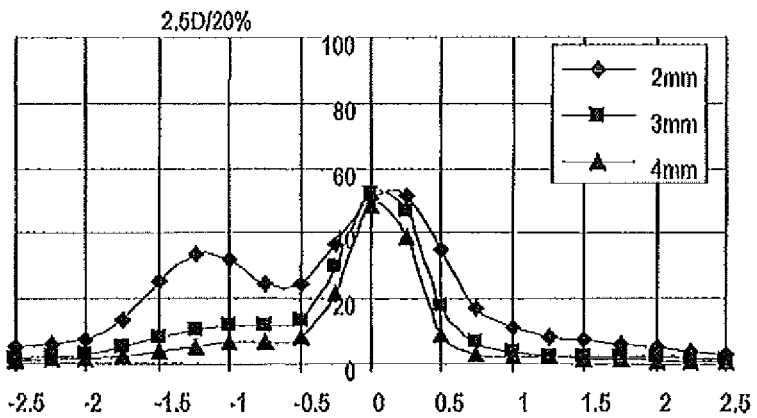
Figure 12A:
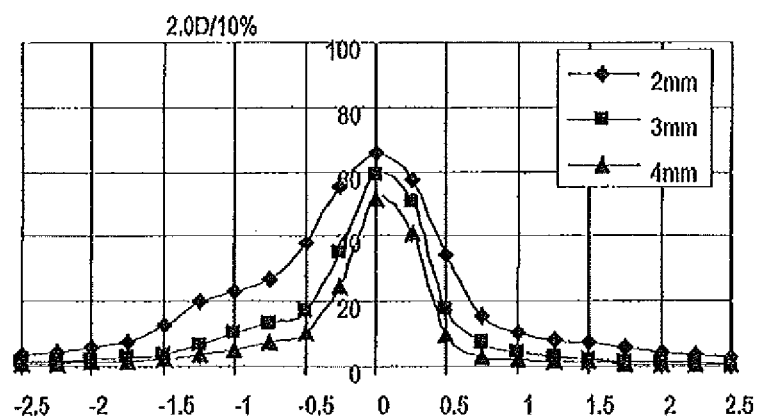
FIGS. 12A-12C illustrate aspects of design profile evaluation according to embodiments of the present invention.
Figure 12B:
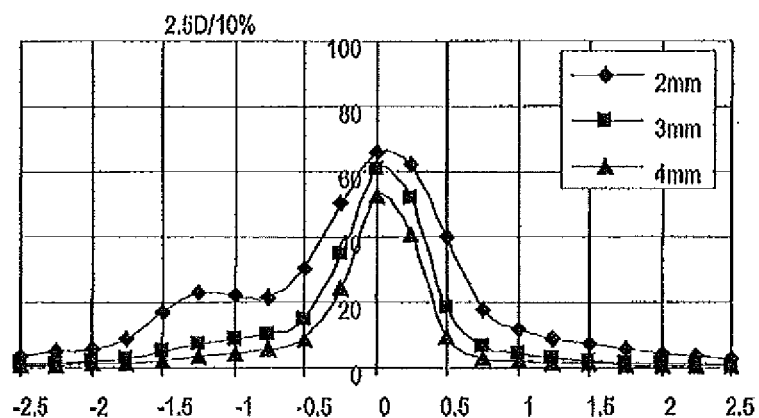
Figure 12C:
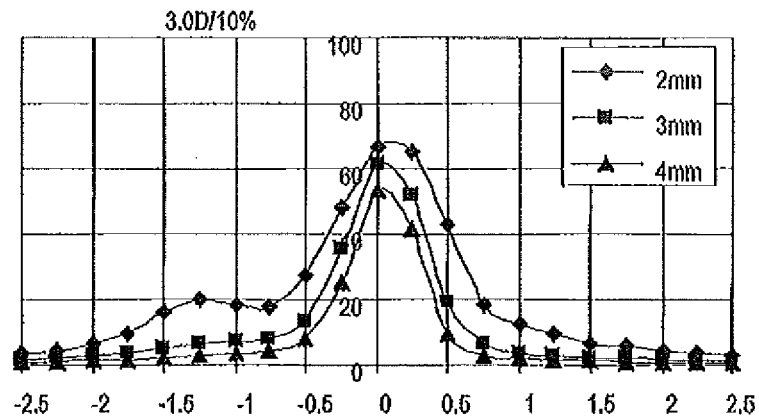
Figure 13A:
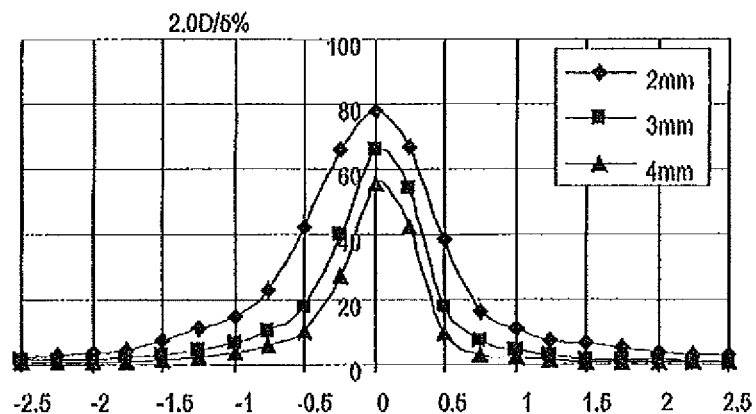
FIGS. 13A-13C illustrate aspects of design profile evaluation according to embodiments of the present invention.
Figure 13B:
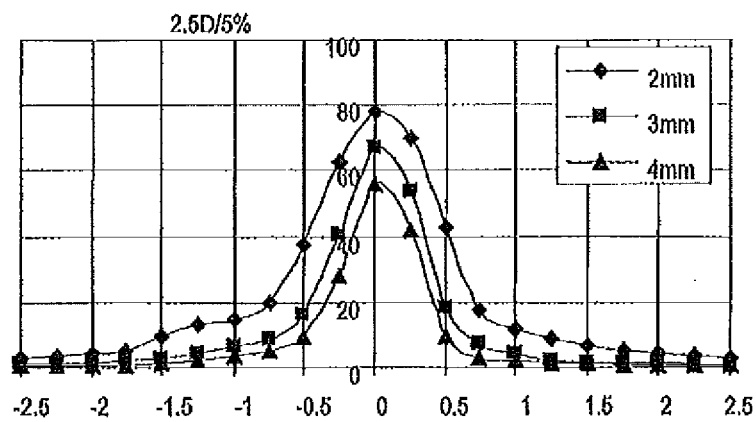
Figure 13C:
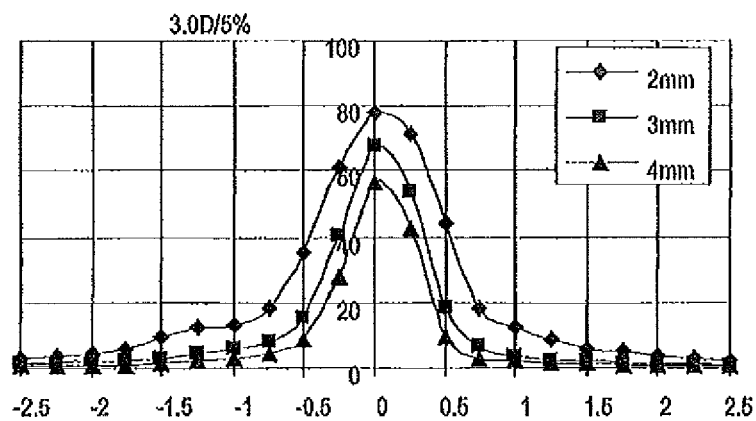
Figure 14A:
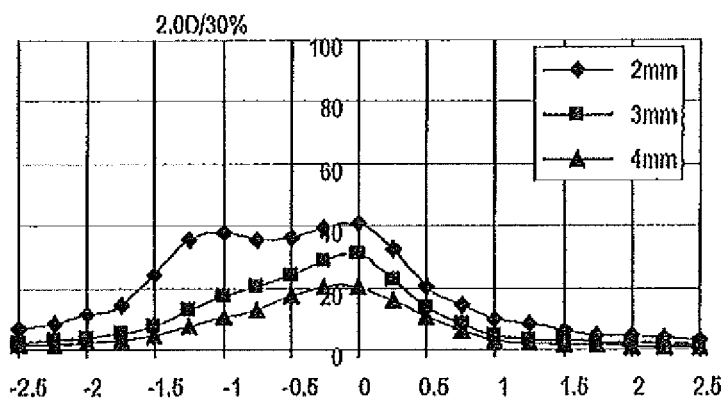
FIGS. 14A-14C illustrate aspects of design profile evaluation according to embodiments of the present invention.
Figure 14B:
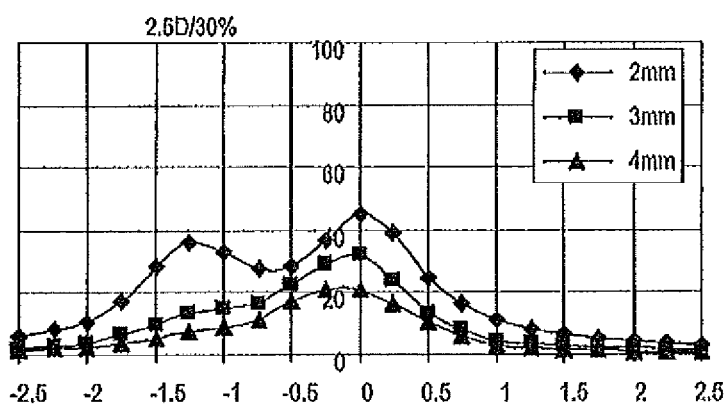
Figure 14C:
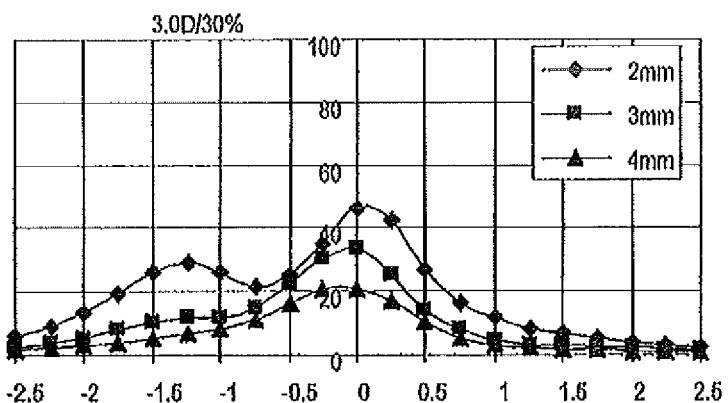
Figure 15A:
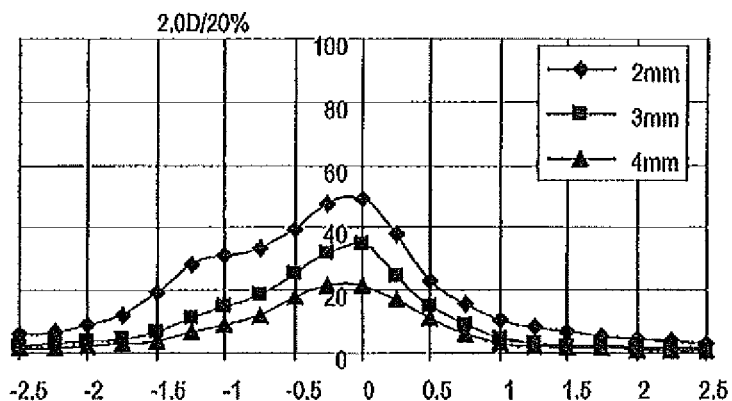
FIGS. 15A-15C illustrate aspects of design profile evaluation according to embodiments of the present invention.
Figure 15B:
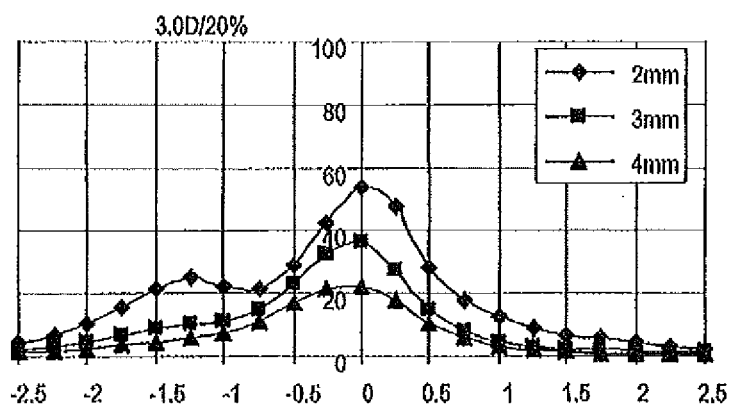
Figure 15C:
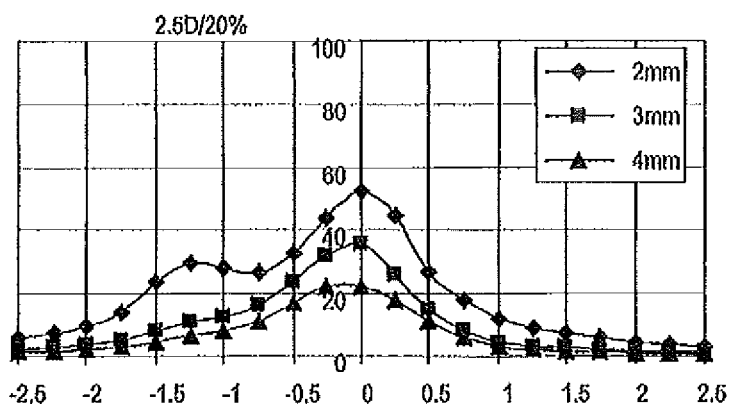
Figure 16A:
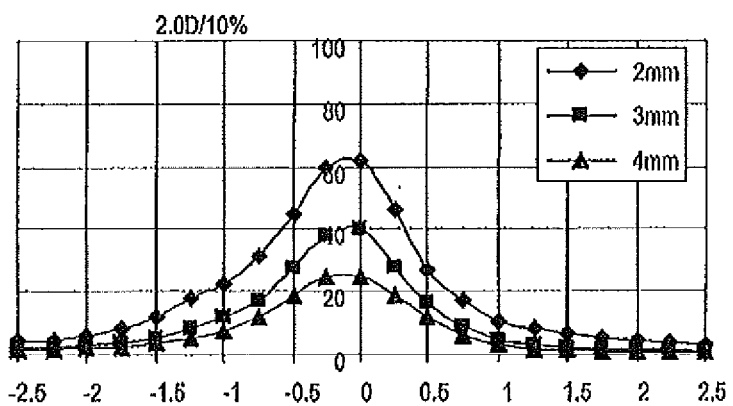
FIGS. 16A-16C illustrate aspects of design profile evaluation according to embodiments of the present invention.
Figure 16B:
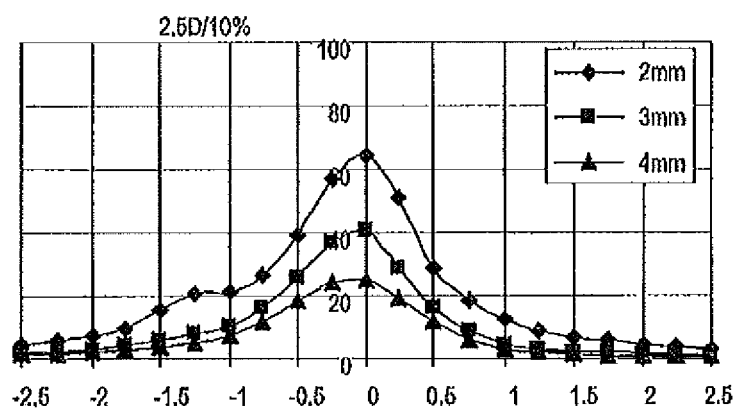
Figure 16C:
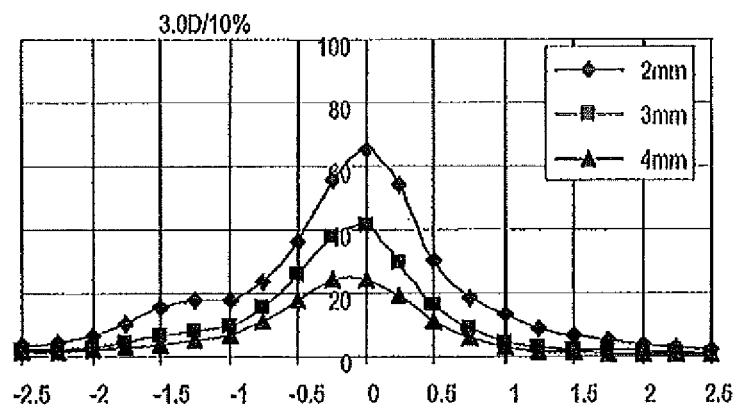
Figure 17A:
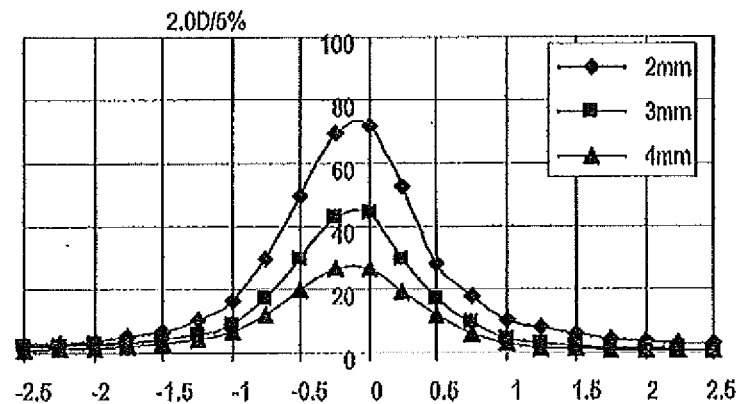
FIGS. 17A-17C illustrate aspects of design profile evaluation according to embodiments of the present invention.
Figure 17B:
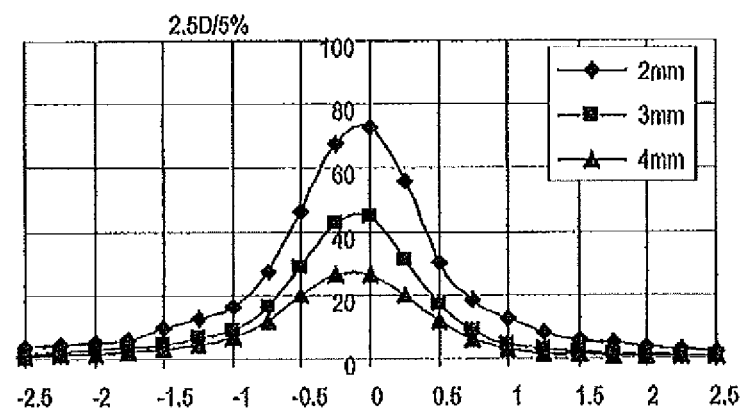
Figure 17C:
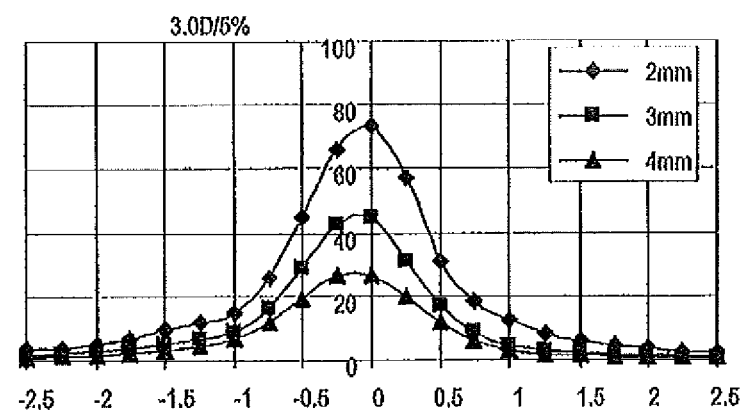

FIGS. 5A-5C can serve as a reference. FIG. 5A shows a regular aspherical design, correcting the corneal spherical aberration. FIG. 5B shows a regular spherical design. FIG. 5C shows a regular diffractive multifocal design, having a 4-diopter add power. It should be noted that the diffractive multifocal IOL of FIG. 5C has a second peak, that is not shown, as it is outside the horizontal scale of the graph. The second peak is similar to the first peak in shape, height, and width.

The horizontal (x-) axis denotes the amount of defocus, expressed in diopters of spectacle power. The left half of the figures, corresponding to minus spectacle powers, represent the situation in which the spectacle makes the eye myopic. The right half of the figure, corresponding to positive spectacle power, represents the situation in which the spectacle makes the eye hyperopic. The vertical (y-) axis denotes image quality, presented by the volume under the white-light MTF curve, as a percentage of the volume under the white-light diffraction limited MTF. As such, it is used as a measure of retinal image quality. The left part of the figure represents the image quality for near and intermediate vision, corresponding to spectacle powers up to −2.5 D.

As illustrated FIGS. 6A, 7A, 8A, and 9A, an echelette design representing a 0.5 D add may provide little benefit over a regular monofocal lens. Other designs indicate some benefit by having an extended depth of focus for at least some of the pupil sizes. None of the single echelette designs, although their echelette is designed as having an add power, show two fully separated peaks (with zero MTF Volume in-between the peaks), such as for the multifocal IOL shown in FIG. 5C. Many designs, although their echelette is designed as having an add power, do not show two separate peaks in the defocus curve, as would be typical for multifocal designs. For example, FIGS. 12A, 13A, 13B, and 13C, while having an increased depth of focus, that is, the volume under the white-light MTF curve is larger than zero for an increased range of defocus values, demonstrate a continuous decreasing image quality when changing the defocus from zero diopter to −2.5 D. Other options show a tendency toward this behavior, having only a very limited dip in the image quality between the peaks representing zero and first order focus, for example those referenced in FIGS. 10A, 11A-C, and 12B-C. For these examples, this small dip in image quality is only present for the smaller pupil size (2.0 mm). Some options demonstrate an image quality in far vision that is independent of pupil size, for example those referenced in FIGS. 8D, 9D, 10A-C, and 11A-C.

FIGS. 14A to 17C illustrate further evaluations of the profile designs referenced in FIGS. 10A to 12C, in a computer model of a "physical eye" of an actual patient. This computer model incorporates optical higher order aberrations from the cornea of the patient. The methodology of the eye model is described in: Piers, P. A., Weeber, H. A., Artal, P. & Norrby, S. "Theoretical comparison of aberration-correcting customized and aspheric intraocular lenses" J Refract Surg 23, 374-84 (2007), the content of which is incorporated herein by reference. The "physical eye" model is associated with a better prediction of the optical performance of IOL designs in the patient.

Figure 18A:
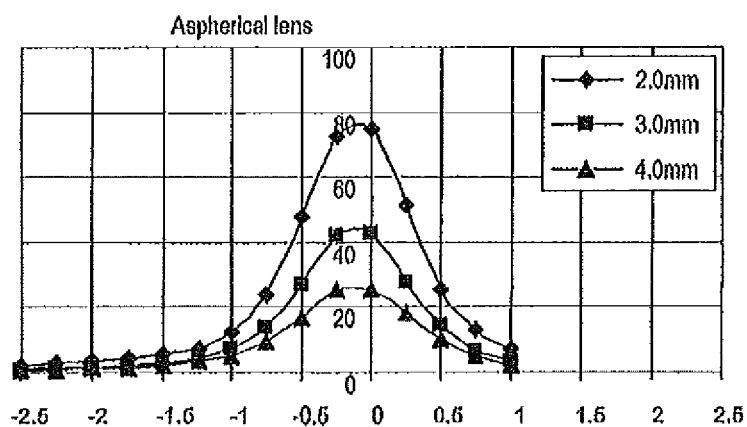
FIGS. 18A-18C show aspects of designs according to embodiments of the present invention.
Figure 18B:
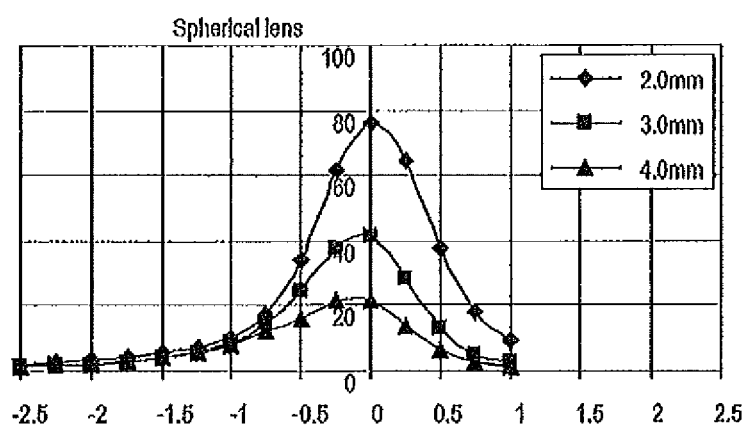
Figure 18C:
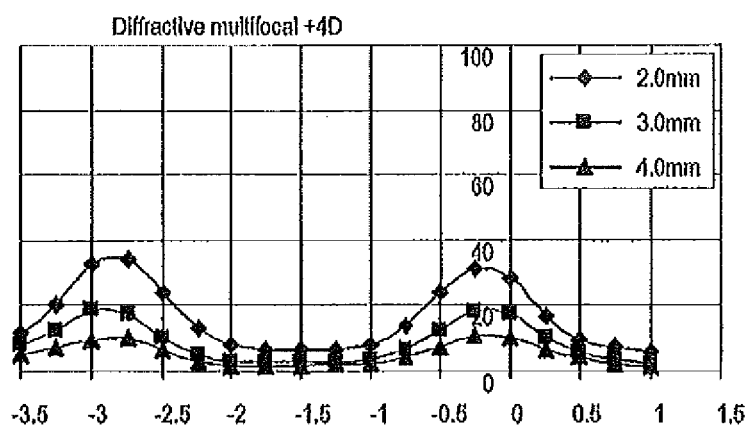

The profile designs involve a single ring diffractive lens according to embodiments of the present invention. These graphical illustrations depict characteristics of image quality associated with defocus curves. FIGS. 14A to 17C can be described as one set. In this series, the size of the echelette is being varied from about 1.2 mm to 1.5 mm in diameter, and the step height is being varied from 0.6 to 1.7 µm. The echelette geometry in this series is characterized in terms xD/y %. The general lens configuration was an equi-biconvex optic, having a Tecnis aspherical anterior surface and a spherical posterior surface. The single ring design was applied onto the posterior surface. The design profiles were assessed for a 2 mm pupil, a 3 mm pupil, and a 4 mm pupil. FIGS. 18A through 18C can be described as the reference.

FIG. 18A shows a regular aspherical design, correcting the corneal spherical aberration. The evaluation of this design profile is assessed for a 2 mm pupil, a 3 mm pupil, and a 4 mm pupil. FIG. 18B shows a regular spherical design. The evaluation of this spherical IOL design profile is assessed for a 2 mm pupil, a 3 mm pupil, and a 4 mm pupil. FIG. 18C can be characterized as a diffractive multifocal+4 D, similar to that described in FIG. 5C.

According to some embodiments, general trends as seen in the ACE model are also valid in the physical eye model. Many designs exhibit an extended depth of focus, when compared to the regular monofocal IOLs. Where there is a dip in the image quality between the far and near focus, for example at FIG. 10A versus FIG. 14A, FIG. 11A versus FIG. 15A, FIG. 11B versus FIG. 15B, FIG. 11C versus FIG. 15C, FIG. 12B versus FIG. 16B, and FIG. 12C versus FIG. 16C, the magnitude of this dip is reduced. The results indicate that these options deliver a certain image quality over a range of distances, without dropping significantly at some intermediate distance.

As illustrated in the figures, a lens may provide an MTF volume of at least about 35% throughout a range from about −1.25 to about 0.25 for a 2.0 mm pupil. In other words, a lens can provide an MTF volume of at least 35% over a continuous range of at least about 1.5 D for a 2.0 mm pupil. Certain embodiments of the present invention provide for an MTF volume of at least 35% over a continuous range of at least about 0.75 D. Other embodiments can provide an MTF volume of at least 35% over a continuous range of at least about 1.0 D. More preferably, embodiments can provide an MTF volume of at least 35% over a continuous range of at least 1.25 D.

Figure 19A:
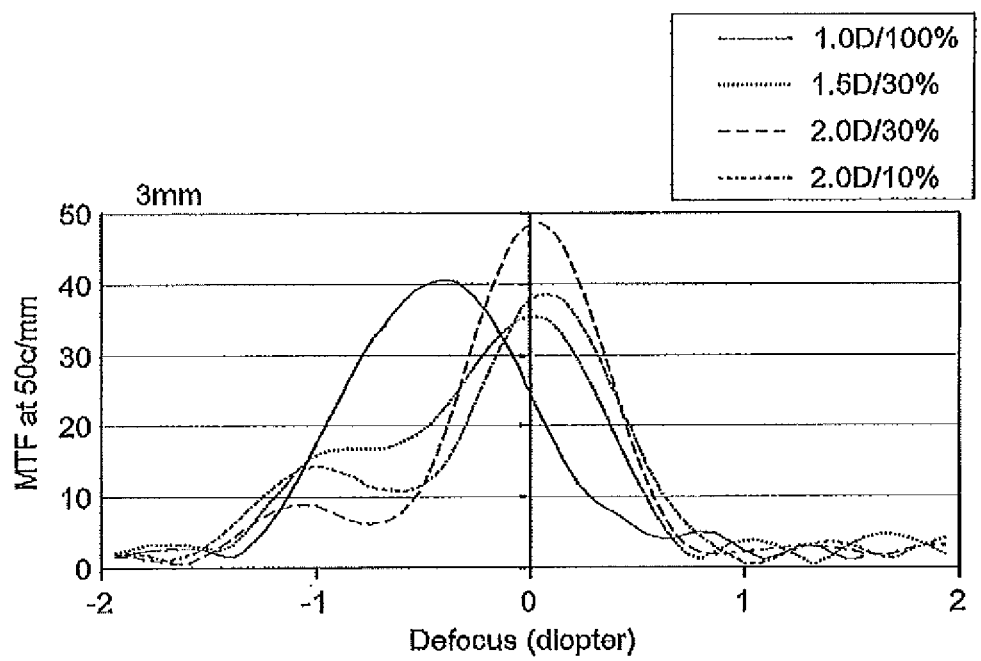
FIGS. 19A and 19B show aspects of measured defocus curves according to embodiments of the present invention.
Figure 19B:
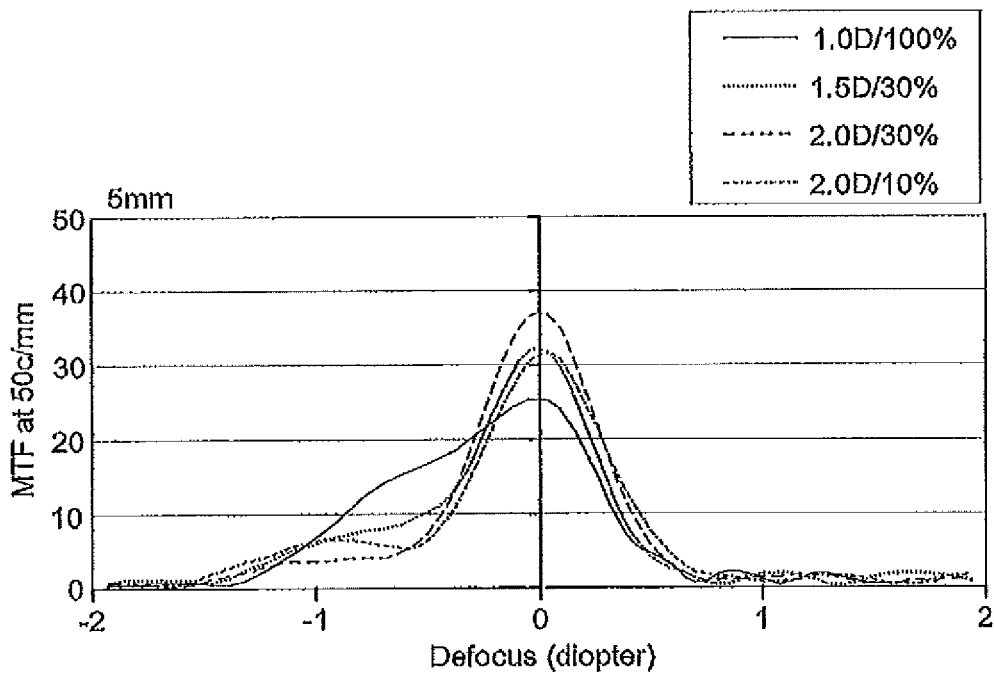

FIGS. 19A and 19B show measured defocus curves of samples pertaining to a 3 mm pupil (FIG. 19A) and a 5 mm pupil (FIG. 19B). These samples correspond to single ring IOL, or single ring echelette, similar to that described in FIGS. 21 and 22. The horizontal axis denotes the defocus value in the spectacle plane, in diopters. The vertical axis denotes the modulus (MTF) at 50 cycles per millimeter. The graphs demonstrate that the actual lenses, as made according to the respective designs, exhibit the extension of the depth of focus at minus defocus values. As illustrated in the figures, a lens may provide an MTF at 50 cycles per millimeter of at least about 15 throughout a range from about −1.0 to about 0.5 for a 3.0 mm pupil. In other words, a lens can provide an MTF at 50 cycles per millimeter of at least 15 over a continuous range of at least about 1.5 D for a 3.0 mm pupil. Certain embodiments provide an MTF at 50 cycles per millimeter of at least 15 over a continuous range of at least 1.0 D.

Figure 20A:
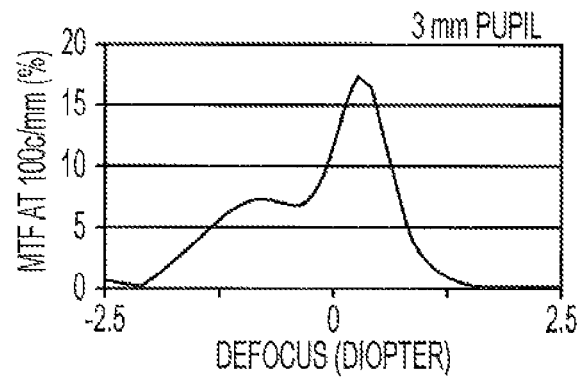
FIGS. 20A-20C show aspects of measured defocus curves according to embodiments of the present invention.
Figure 20B:
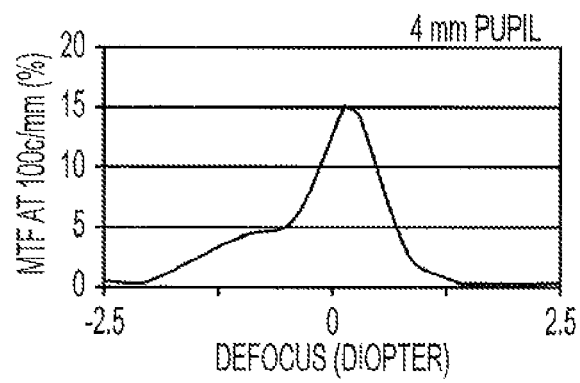
Figure 20C:
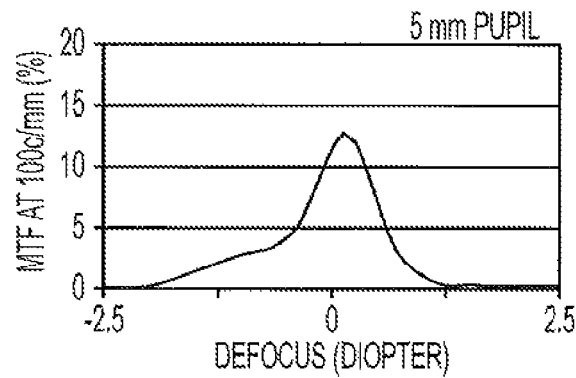

FIGS. 20A-20C show measured defocus curves in the ACE eye model of an exemplary embodiment disclosed in section 4 with a ring diameter of 1.21 mm and a phase delay of ½ wavelength. The horizontal axis denotes the defocus value in the spectacle plane, in diopters. The vertical axis denotes the modulus (MTF) at 100 cycles per millimeter. Data for 3 mm, 4 mm, and 5 mm pupil diameters are included. As illustrated in the figures, a lens may provide an MTF at 100 cycles per millimeter of at least about 7 throughout a range from about −1.0 to about 0.8 for a 3.0 mm pupil. In other words, a lens can provide an MTF at 100 cycles per millimeter of at least 7 over a continuous range of at least about 1.8 D for a 3.0 mm pupil. Certain embodiments provide an MTF at 100 cycles per millimeter of at least 7 over a continuous range of at least 1.5 D. The graphs demonstrate that the actual lenses, as made according to the respective designs, exhibit the extension of the depth of focus.

Figure 21:
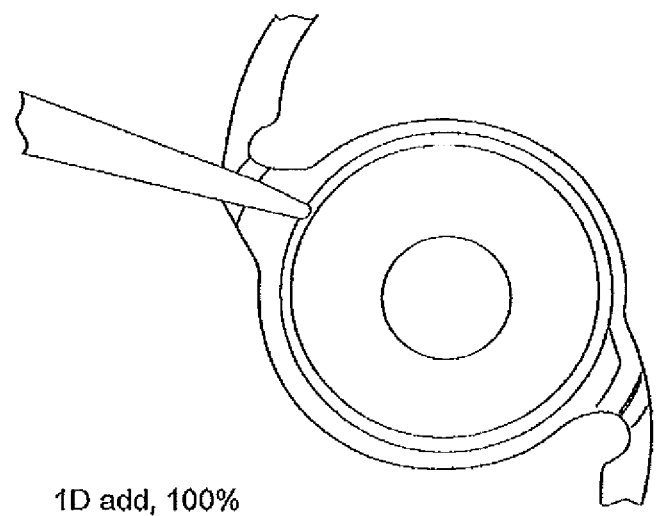
FIG. 21 depicts aspects of a diffractive single ring IOL according to embodiments of the present invention.
Figure 22:
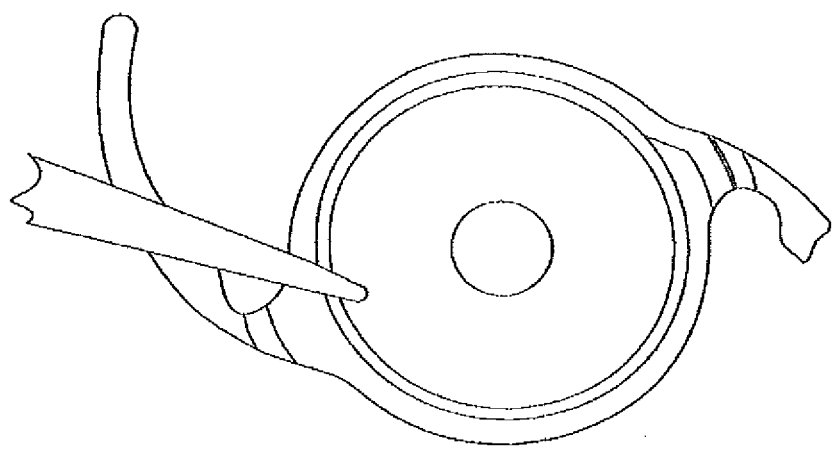
FIG. 22 depicts aspects of a diffractive single ring IOL according to embodiments of the present invention.

FIG. 21 shows an exemplary diffractive single ring IOL wherein the geometry is characterized by a 1.0 D/100% design profile. FIG. 22 shows an exemplary diffractive single ring IOL wherein the geometry is characterized by a 2.0 D/10% design profile.

The term single microstructure can refer to the fact that, when viewed macroscopically, for example as shown in FIGS. 21-22, just one single ring is visible on the surface. In other words, there is one optical phase transition on the whole optical surface. Optionally, the term single microstructure can refer to the fact that the lens has only one single echelette, represented by the inner portion of the lens surface. In alternative embodiments, the single echelette is an annulus around a central portion of the lens. An annulus echelette can have two phase transitions, one at the inner radius of the echelette, and one at the outer radius of the echelette.

IOLs such as the exemplary embodiments depicted in FIGS. 21-22 can be made of an acrylic material. An echelette can be placed on the posterior or anterior surface, and the peripheral zone may be aspherical. The opposing surface may be aspherical (e.g. correcting corneal spherical aberration).

Table 4 below provides dimensions of various samples, where De represents the diameter of the ring, or echelette, in millimeters, and stepheight represents the height of the profile, in µm. As in Table 3 above, the single echelette design geometry is characterized in terms of conventional diffractive IOL nomenclature regarding add power and percentage of light. The lenses were tested in the ACE model, using white light.

TABLE 4

| Name | De (mm) | step height (µm) |
|---|---|---|
| 1.0D/100% | 2.10 | 3.7 |
| 1.5D/30% | 1.71 | 1.7 |
| 2.0D/30% | 1.48 | 1.7 |
| 2.0D/10% | 1.48 | 1.0 |

Figures 1, 23A:
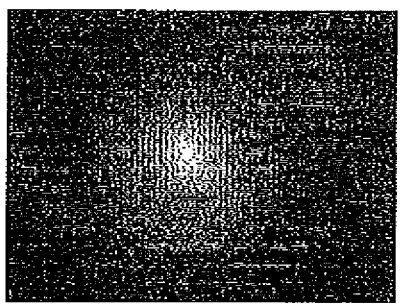
Figures 1, 23B:
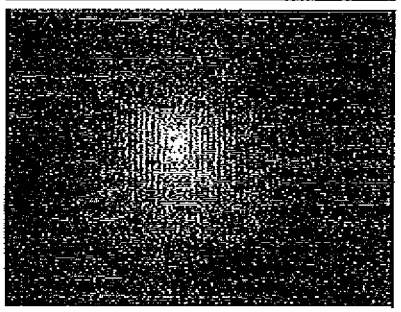
Figures 1, 23C:
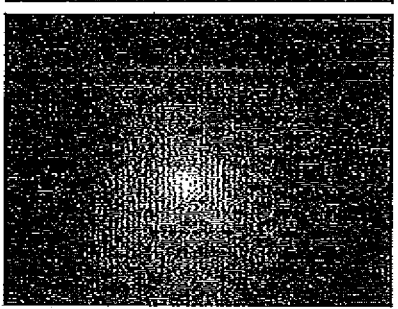
Figures 1, 23D:
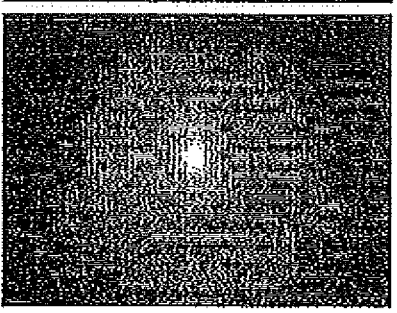

FIGS. 23A-1 to 23D-2 and 24 show measured performance of dysphotopsia (e.g. halo effects) of samples for a 4.0 mm pupil, in an ACE eye model. These figures are based on the image of an extended light source of white light, representing the headlight of a car at a distance of about 50 meters, and correspond to IOL samples, or measurements on real lenses. FIG. 23A-1 shows the image generated by the light source, illustrating the appearance of the halo of a 2.0 D/30% design. FIG. 23B-1 shows the image of an aspherical monofocal. FIG. 23C-1 shown the image of a refractive bifocal lens with a +1 D add power. FIG. 23D-1 shows the image of a diffractive multifocal lens with a 4 D add power.

These figures demonstrate that the amount of halo of the 2.0 D/30% design, as shown in FIG. 23A-1, is reduced as compared to a diffractive multifocal lens as shown in FIG. 23D-1, and as compared with a refractive bifocal lens with 1 D add power as shown in FIG. 23C-1. FIGS. 23A-2, 23B-2, 23C-2, and 23D-2 provide negative images of FIGS. 23A-1, 23B-1, 23C-1, and 23D-1, respectively, for better visibility.

Figure 24:
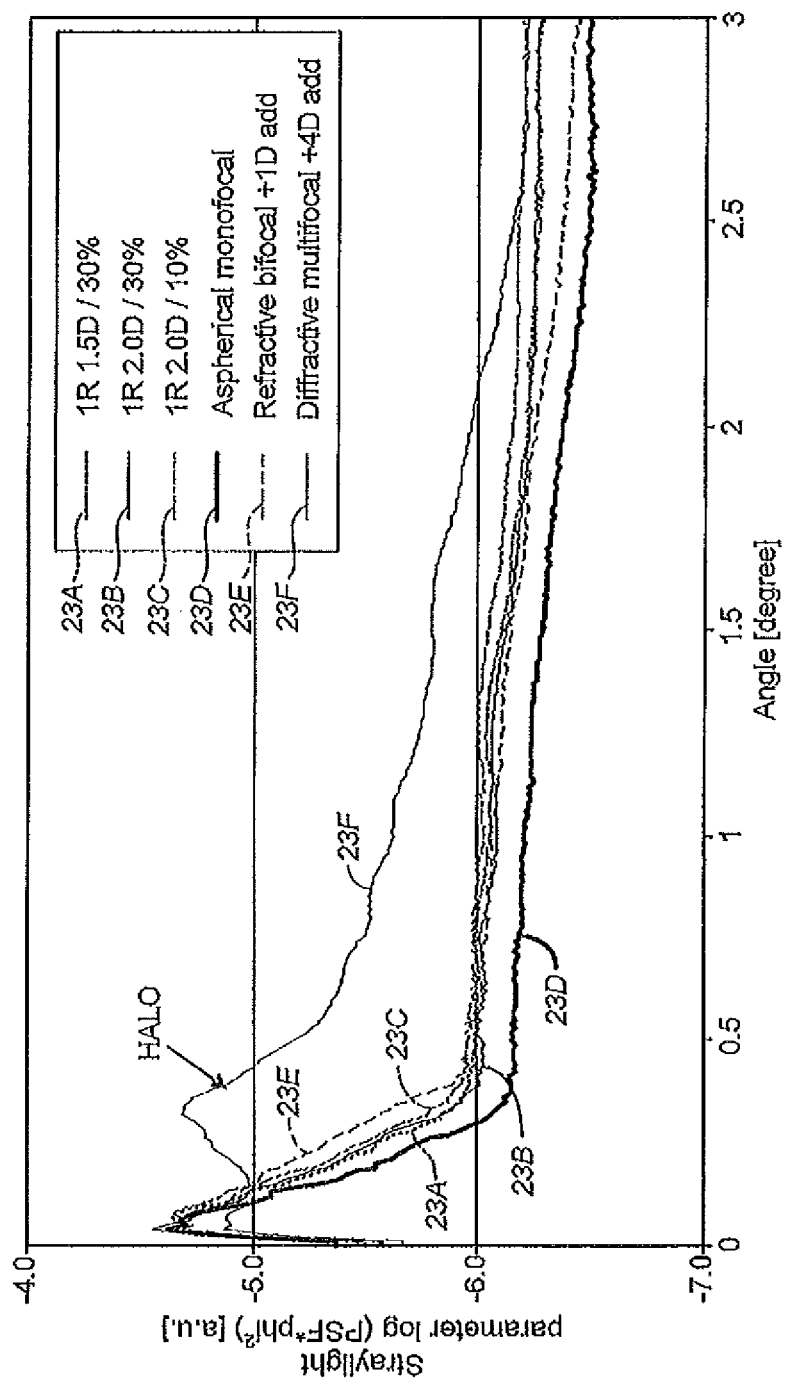
FIG. 24 shows aspects of dysphotopsia performance according to embodiments of the present invention.

FIG. 24 shows a graphical representation of the measured light scatter (straylight) corresponding to the light source images of FIGS. 23A-1, 23B-1, 23C-1, and 23D-1. The horizontal axis denotes the visual angle, in degrees, and the vertical axis denotes the amount of scatter, represented by the scatter parameter. The scatter parameter is defined as the logarithm of the light energy times the square of the visual angle. The size of the halo, as shown in FIGS. 37A-1, 37B-1, 37C-1, and 37D-1 in the straylight graph of FIG. 24 is between zero and about 0.5 degrees. The peak is part of the halo. In other words, pure straylight is measured for visual angles above 0.5 degrees. The vertical axis has arbitrary units. FIG. 24 shows the straylight of the 1.5 D/30% design (line 23A), the 2.0 D/30% design (line 23B), and the 2.0 D/10% design (line 23C). The amount of straylight is substantially the same for these three designs. For reference FIG. 24 also shows the straylight image corresponding to an aspherical monofocal (line 23D), as well as a refractive bifocal lens with a +1 D add power (line 23E), and a diffractive multifocal lens with a 4 D add power (line 23F). FIG. 24 shows that the amount of straylight of the 3 designs having a single echelette is smaller than that of the diffractive multifocal lens, and just slightly higher than that of a regular monofocal lens. FIG. 24 also confirms the conclusion from FIGS. 23A-1 to 23D-2 that a design having a single echelette does not produce any significant halos.

While the examples above describe a parabolic echelette, an echelette and outer zone design may be configured so as to reduce the amount of light in predetermined non-functional diffractive orders. Additional aspects of these features are described in previously incorporated U.S. patent application Ser. No. 12/429,155 filed Apr. 23, 2009. Using the same principles as set forth in the aforementioned application, the amount of light in other diffractive orders can be enhanced, as to aid viewing using those diffractive orders.

Embodiments of the present invention may be combined with a multifocal lens design, and with that extend the depth of focus of each focus of the multifocal lens. Similarly, embodiments of the present invention may be combined with an accommodating lens design, by which the range of accommodation of the accommodating lens can be extended. In addition, embodiments of the present invention may be combined with lenses correcting ocular aberrations, like toric lenses, aspherical lenses, lenses correcting chromatic aberrations, and the like. Embodiments for correcting chromatic aberrations may, for example, increase the phase delay of the echelettes by a discrete multiple of wavelengths. For example, in the preceding example in which a phase delay of 0.5 was used, corresponding to a stepheight of 2.05 µm, an alternative embodiment may have a phase delay of 1.5, corresponding to a stepheight of 6.15 µm. This embodiment thus directs the first order diffraction to the far focus, and the second order diffraction establishes the depth of focus at the intermediate and near range.

While the exemplary embodiments have been described in some detail, by way of example and for clarity of understanding, those of skill in the art will recognize that a variety of modification, adaptations, and changes may be employed. Hence, the scope of the claims should not be limited to the description of the preferred versions contained herein.

What is claimed is:

1. An ophthalmic lens comprising:
    an anterior face and a posterior face, the faces disposed about an optical axis;
    a central echelette imposed on the anterior or the posterior face;
    a central zone; and
    a peripheral zone that surrounds the central echelette,
    wherein the lens provides an MTF volume of at least about 35% over a continuous range of diffractive power of at least about 0.75 D.

2. The ophthalmic lens of claim 1, wherein one or both of the anterior and the posterior face have a diffractive profile.

3. The ophthalmic lens of claim 1, wherein one or both of the anterior and the posterior face have a toric profile.

4. The ophthalmic lens of claim 1, wherein the central echelette is disposed within the central zone of the lens.

5. The ophthalmic lens of claim 1, wherein the central echelette surrounds the central zone of the lens.

6. The ophthalmic lens of claim 1, wherein the central echelette is characterized by a constant phase shift.

7. The ophthalmic lens of claim 1, wherein the central echelette is characterized by a surface area between 1 and 7 square millimeters.

8. The ophthalmic lens of claim 7, wherein the central echelette has a diameter within a range from about 1 mm to about 5 mm.

9. The ophthalmic lens of claim 1 wherein the central echelette is characterized by a parabolic curve.

10. The ophthalmic lens of claim 1, wherein the lens further comprises a peripheral portion characterized by a spherical curve or an aspherical curve.

11. The ophthalmic lens of claim 10, wherein the peripheral portion has a refractive profile.

12. The ophthalmic lens of claim 1, wherein the ophthalmic lens comprises a transition characterized by a step height having a value within a range from about 0.5 µm and about 4 µm.

13. The ophthalmic lens of claim 12, wherein the step height provides a phase shift between about 0.25 and about 3 times the design wavelength.

14. The ophthalmic lens of claim 1, wherein the ophthalmic lens provides an MTF at 50 cycles per millimeter of at least about 15 over a continuous range of diffractive power of at least about 1.5 D for a 3.0 mm pupil.

15. The ophthalmic lens of claim 1, wherein the ophthalmic lens provides an MTF at 100 cycles per millimeter of at least about 7 over a continuous range of diffractive power of at least about 1.8 D for a 3.0 mm pupil.

* * * * *